(12) United States Patent
Tamura et al.

(10) Patent No.: US 10,308,574 B2
(45) Date of Patent: Jun. 4, 2019

(54) REDUCTION CATALYST AND CHEMICAL REACTOR

(71) Applicant: KABUSHIKI KAISHA TOSHIBA, Minato-ku (JP)

(72) Inventors: Jun Tamura, Tokyo (JP); Satoshi Mikoshiba, Yamato (JP); Yuki Kudo, Yokohama (JP); Akihiko Ono, Tokyo (JP); Ryota Kitagawa, Tokyo (JP); Masakazu Yamagiwa, Yokohama (JP); Eishi Tsutsumi, Kawasaki (JP); Yoshitsune Sugano, Kawasaki (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 0 days.

(21) Appl. No.: 15/698,394

(22) Filed: Sep. 7, 2017

(65) Prior Publication Data

US 2017/0369405 A1  Dec. 28, 2017

Related U.S. Application Data

(63) Continuation of application No. PCT/JP2016/064187, filed on May 12, 2016.

(30) Foreign Application Priority Data

May 21, 2015 (JP) ................................. 2015-103684

(51) Int. Cl.
*B01J 27/24* (2006.01)
*C07C 29/136* (2006.01)
(Continued)

(52) U.S. Cl.
CPC ............. *C07C 29/136* (2013.01); *B01J 27/24* (2013.01); *B01J 31/26* (2013.01); *B01J 31/28* (2013.01);
(Continued)

(58) Field of Classification Search
None
See application file for complete search history.

(56) References Cited

U.S. PATENT DOCUMENTS

| 4,513,141 A | 4/1985 | Brunelle et al. |
| 4,605,745 A | 8/1986 | Brunelle et al. |

(Continued)

FOREIGN PATENT DOCUMENTS

| JP | 60-4134 | 1/1985 |
| JP | 2-1704 | 1/1990 |

(Continued)

OTHER PUBLICATIONS

International Search Report dated Jun. 21, 2016 in PCT/JP2016/064187, filed on May 12, 2016 (with English Translation).

(Continued)

*Primary Examiner* — Medhanit W Bahta
(74) *Attorney, Agent, or Firm* — Oblon, McClelland, Maier & Neustadt, L.L.P.

(57) ABSTRACT

According to one embodiment, a reduction catalyst includes a current collector including a metal layer; and organic molecules including a quaternary nitrogen cation, which are bonded to the metal layer. The organic molecules are represented by any of the following general formulae I to V.

General formula I (Continued)

General formula II

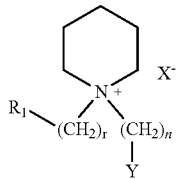

General formula III

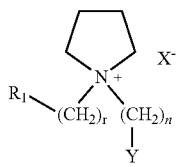

General formula IV

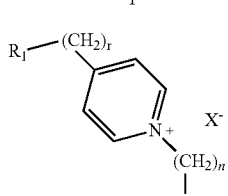

General formula V

13 Claims, 7 Drawing Sheets

(51) Int. Cl.
| C07C 29/14 | (2006.01) |
| C07C 29/15 | (2006.01) |
| C07C 29/153 | (2006.01) |
| C07C 31/20 | (2006.01) |
| B01J 31/26 | (2006.01) |
| B01J 31/28 | (2006.01) |
| B01J 31/38 | (2006.01) |
| C25B 3/04 | (2006.01) |
| C07C 211/62 | (2006.01) |
| C07D 233/54 | (2006.01) |
| C25B 1/00 | (2006.01) |
| C25B 1/04 | (2006.01) |
| C25B 9/08 | (2006.01) |
| G01N 23/2273 | (2018.01) |
| G01N 21/35 | (2014.01) |
| H01J 37/28 | (2006.01) |

(52) U.S. Cl.
CPC ............ *B01J 31/38* (2013.01); *C07C 29/15* (2013.01); *C07C 211/62* (2013.01); *C07D 233/54* (2013.01); *C25B 1/00* (2013.01); *C25B 1/003* (2013.01); *C25B 1/04* (2013.01); *C25B 3/04* (2013.01); *C25B 9/08* (2013.01); *C07C 29/14* (2013.01); *C07C 29/153* (2013.01); *G01N 23/2273* (2013.01); *G01N 2021/3595* (2013.01); *H01J 37/28* (2013.01); *Y02E 60/366* (2013.01)

(56) References Cited

U.S. PATENT DOCUMENTS

| 5,906,722 | A | 5/1999 | Foller et al. |
| 6,399,202 | B1 | 6/2002 | Yu et al. |
| 2003/0019758 | A1 | 1/2003 | Gopal |
| 2010/0209814 | A1 | 8/2010 | Suzuki et al. |
| 2012/0277465 | A1 | 11/2012 | Cole et al. |
| 2012/0292199 | A1 | 11/2012 | Deguchi et al. |
| 2012/0308903 | A1 | 12/2012 | Masel |
| 2015/0252482 | A1 | 9/2015 | Ono et al. |
| 2015/0252483 | A1 | 9/2015 | Ono et al. |
| 2016/0076158 | A1 | 3/2016 | Tamura et al. |
| 2016/0376717 | A1 | 12/2016 | Tamura et al. |
| 2017/0073827 | A1* | 3/2017 | Tamura .................. C25B 15/08 |

FOREIGN PATENT DOCUMENTS

| JP | 2-83364 | 3/1990 |
| JP | 2003-515872 | 5/2003 |
| JP | 2001-514956 | 9/2004 |
| JP | 2010-188243 | 9/2010 |
| JP | 2011-94194 | 5/2011 |
| JP | 2014-101550 | 6/2014 |
| JP | 2014-101551 | 6/2014 |
| JP | 2014-518335 | 7/2014 |
| JP | 2015-132012 | 7/2015 |
| JP | 2015-175020 | 10/2015 |
| WO | WO 2009/133846 A1 | 11/2009 |
| WO | WO 2011/132375 A1 | 10/2011 |
| WO | WO 2012/006240 A1 | 1/2012 |
| WO | WO 2014/192891 A1 | 12/2014 |

OTHER PUBLICATIONS

Written Opinion dated Jun. 21, 2016 in PCT/JP2016/064187, filed on May 12, 2016.
Barbara Ballarin, et al., "A new gold(III)-aminoethyl imidazolium aurate salt as precursor for nanosized Au electrocaralysts", ElectrochemicaActa, vol. 56, 2010, pp. 11.
Shagayegh Saadati, et al., "Layer by layer assembly of catalase and amine-terminated ionic liquid onto titanium nitride nanoparticles modified glassy carbon electrode: Study of direct voltammetry and bioelectrocatalytic activity", Analytica Chimica Acta, vol. 753, pp. 10, 2012.
Sun Yu et al., "Photoelectrochemical Reduction of Carbon Dioxide at Si( 111) Electrode Modified by Viologen Molecular Layer with Metal Complex," Chemistry Letters, vol. 41 , No. 3, Mar. 2012, pp. 5.
Yi Zhang, et al, "$CO^2$ Capture by Imidazolate-Based Ionic Liquids: Effect of Functionalized Cation and Dication," Industrial & Engineering Chemistry Research, vol. 52, No. 18, 2013, pp. 4.
Steven Y. Reece, et al., "Wireless Solar Water Splitting Using Silicon-Based Semiconductors and Earth-Abundant Catalysis", Science vol. 334, No. 4, Nov. 2011, pp. 4.
Yoshio Hori, et al., "Electrocatalytic Process of Co Selectivity in Electrochemical Reduction of $CO_2$ at Metal Electrodes in Aqueous Media", Electrochemica Acta., vol. 39, No. 11/12, 1994, pp. 7.
Andrew B. Bocarsly, et al., "Comparative Study of Imidazole and Pyridine Catalyzed Reduction of Carbon Dioxide at Illuminated Iron Pyrite Electrodes," ACS Catalysis, vol. 2, No. 8, 2012, pp. 9.

* cited by examiner

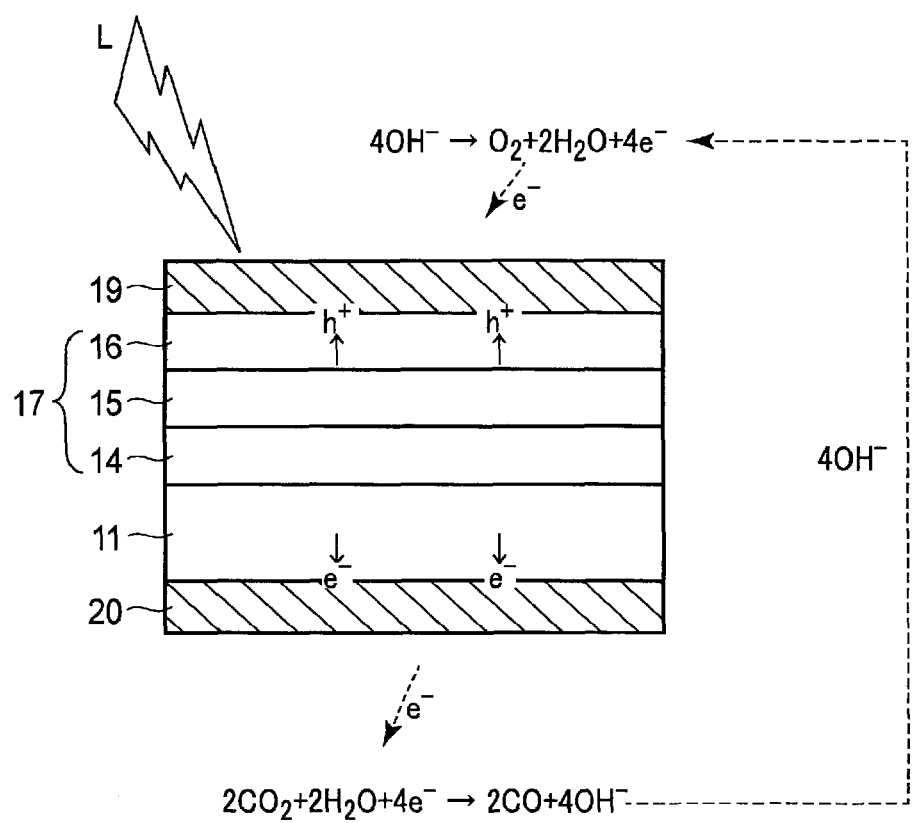
F I G. 7

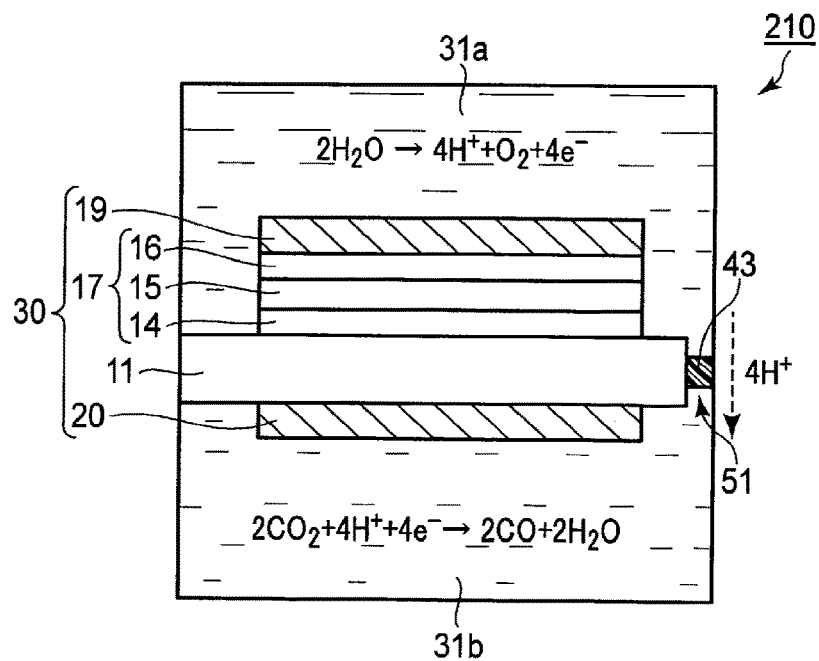
F I G. 10
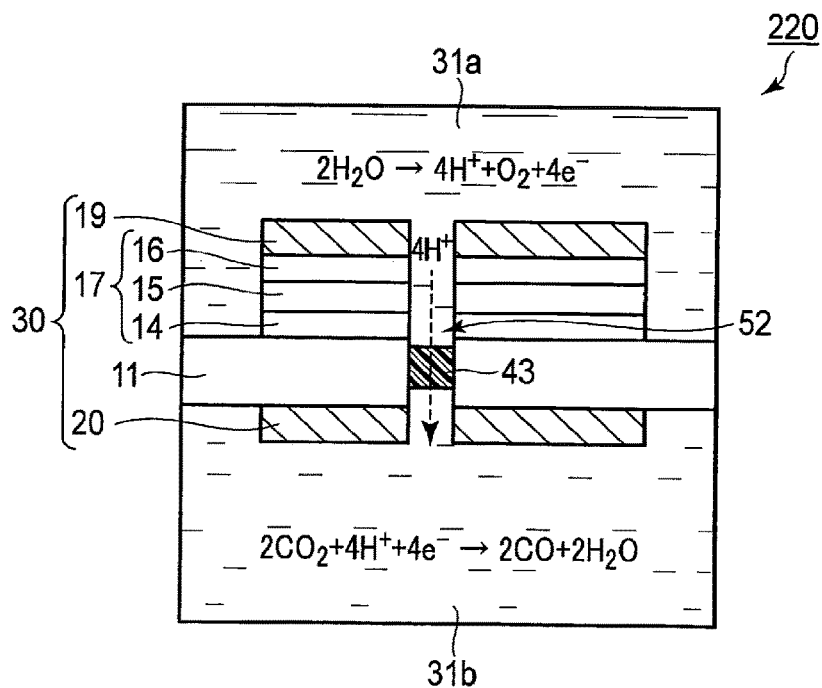
F I G. 11

REDUCTION CATALYST AND CHEMICAL REACTOR

CROSS-REFERENCE TO RELATED APPLICATIONS

This application is a Continuation Application of PCT Application No. PCT/JP2016/064187, filed May 12, 2016 and based upon and claiming the benefit of priority from Japanese Patent Application No. 2015-103684, filed May 21, 2015, the entire contents of all of which are incorporated herein by reference.

FIELD

Embodiments relate to a reduction catalyst and a chemical reactor including the reduction catalyst.

BACKGROUND

From the viewpoint of energy problems and environmental problems, it is required to efficiently reduce $CO_2$ by light energy like plants. Plants use a system, called Z-scheme, which excites light energy in two stages. In a photochemical reaction using this system, water ($H_2O$) is oxidized to obtain electrons, and carbon dioxide ($CO_2$) is reduced to synthesize cellulose or sugars.

Currently, artificial photosynthetic systems which imitate the Z-scheme of such plants have been developed. In the artificial photosynthetic system, a potential necessary for reduction of $CO_2$ is obtained from visible light by using a photocatalyst. However, since energy efficiency of the photocatalyst is low, an artificial photochemical reaction which does not use a sacrificial reagent has a problem that reaction efficiency is very low. Therefore, a $CO_2$ reduction technology with high reaction efficiency is required.

BRIEF DESCRIPTION OF THE DRAWINGS

FIG. 7 is a cross-sectional view showing another example of an operation principle of the photochemical reaction cell of FIG. 5.

FIG. 10 is a cross-sectional view showing a structure of a modification example 1 of the chemical reactor according to the third embodiment.

FIG. 11 is a cross-sectional view showing a structure of a modification example 2 of the chemical reactor according to the third embodiment.

DETAILED DESCRIPTION

<First Embodiment>

A reduction catalyst according to a first embodiment includes a current collector including a metal layer, and organic molecules including a quaternary nitrogen cation, which are bonded to the metal layer and are represented by any of the following general formulae I to V.

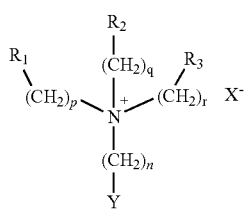

General formula I

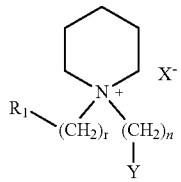

General formula II

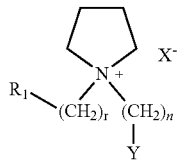

General formula III

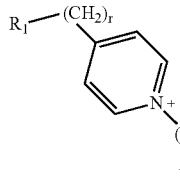

General formula IV

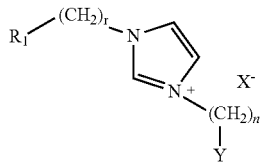

General formula V

In the general formulae I to V, $R_1$ is a primary, secondary, or tertiary amino group. $R_2$ and $R_3$ may be identical to or different from each other and are each independently H or a primary, secondary, or tertiary amino group. p, q, r, and n are each independently an integer from 1 to 12. Y is a reactive functional group, and $X^-$ represents a counter anion.

Figure 1:
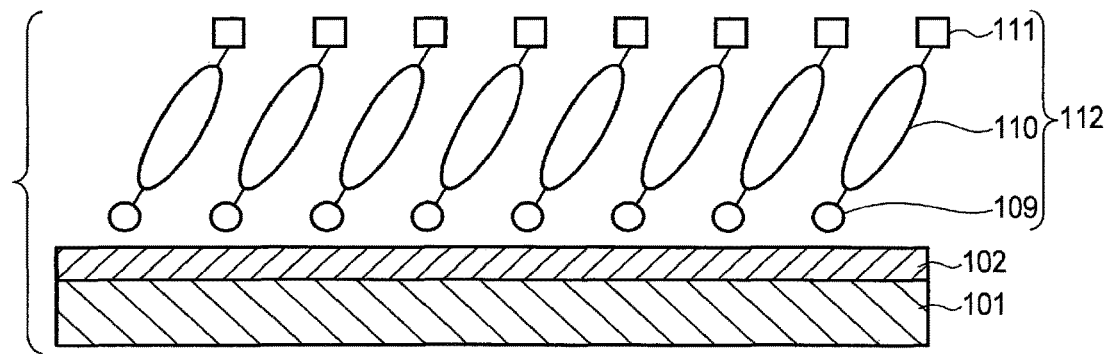
FIG. 1 is a view showing a structure of a reduction catalyst according to a first embodiment.
Figure 2:
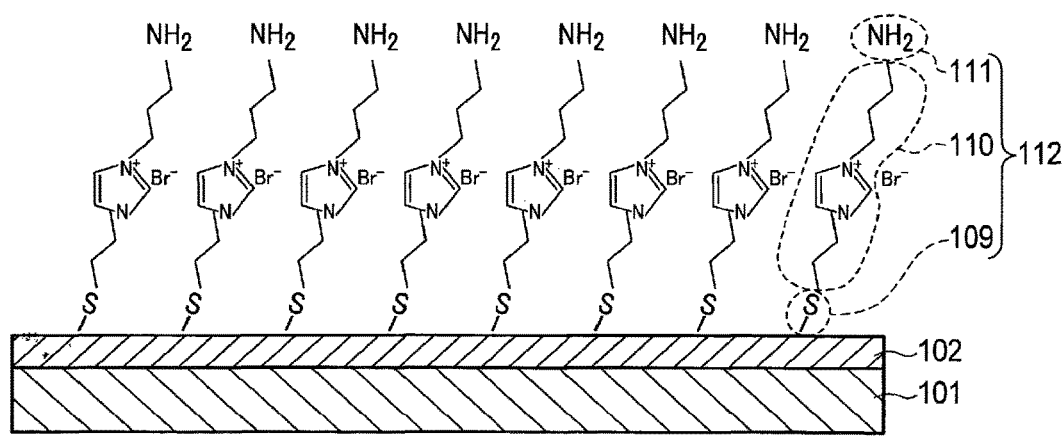
FIG. 2 is a view showing an example of the structure of the reduction catalyst of FIG. 1 in detail.

Hereinafter, the reduction catalyst according to the first embodiment will be described with reference to FIGS. 1 and 2. FIG. 1 is a view showing a structure of a reduction catalyst 1, and FIG. 2 is a view showing an example of the structure of the reduction catalyst 1 in detail. As shown in FIG. 1, the reduction catalyst 1 includes a current collector 101 and organic molecules 112 including a quaternary nitrogen cation. The current collector 101 has a metal layer 102 on the surface thereof. The organic molecules 112 including the quaternary nitrogen cation are bonded to the metal layer 102 to form a monolayer (self-assembled monolayer: SAM)).

The organic molecules including the quaternary nitrogen cation will be referred to as modified organic molecules.

The current collector 101 includes a material having electrical conductivity. As the current collector 101, for example, a stainless steel substrate may be used.

The metal layer 102 on the surface of the current collector 101 includes at least one metal selected from the group consisting of Au, Ag, Cu, Zn, Pt, Fe, Ti, Ni, Sn, In, and Bi. The metal layer 102 may include components other than the metal, but it is preferable that the metal layer 102 includes only a metal. The metal layer 102 and the current collector 101 may include the same material. In this case, the metal constituting the metal layer 102 may also serve as the current collector 101.

The metal included in the metal layer 102 functions as a catalyst which activates the reduction reaction. Since the activity of the catalyst is improved, the metal included in the metal layer 102 is preferably in the state of fine particles.

An average grain size of the metal fine particles included in the metal layer 102 is preferably 1 nm to 300 nm. When the average grain size is 300 nm or less, the activity efficiency of the catalyst can be increased. In addition, it is difficult to produce metal fine particles having an average grain size of less than 1 nm. When the average grain size of the metal fine particles is 150 nm or less, it is more preferable because the activity efficiency of the catalyst is further improved. Note that the metal fine particles may be primary particles having an average grain size of 50 nm or less, but secondary particles obtained by aggregating such primary particles may also be used.

The modified organic molecule 112 includes a skeleton 110 including a quaternary nitrogen cation, a reactive functional group 109 located at one end, and an amino group 111 located at the other end. The quaternary nitrogen cation included in the modified organic molecule 112 is at least one cation selected from an alkylammonium cation, a pyridinium cation, a piperidinium cation, a pyrrolidinium cation, and an imidazolium cation. As described below, it is more preferable that the quaternary nitrogen cation is an imidazolium cation, because the effect of improving the reduction activity is high.

The skeleton 110 includes a quaternary nitrogen cation and an alkyl group which is a substituent on the cation. The number of carbon atoms of the alkyl group corresponds to p, q, r, and n in the general formulae I to V, and is each independently an integer from 1 to 12. In the general formulae I to V, when p, q, r, and n are 1 to 12, the quaternary nitrogen cation and the amino group, and the quaternary nitrogen cation and the metal layer 102 are not too far apart. Thus, as described below, the quaternary nitrogen cation can obtain the effect of improving reduction efficiency. It is more preferably that p, q, r, and n are an integer from 2 to 6.

The reactive functional group 109 corresponds to Y in the general formulae I to V. The reactive functional group 109 has an affinity for the metal layer 102 and is chemically bonded to the metal layer 102. Due to this, the modified organic molecule 112 is fixed to the metal layer 102. The reactive functional group 109 is preferably a functional group which can be covalently bonded to the metal layer 102, and is preferably selected from, for example, a thiol group, a disulfide group, and a thiocyanate group. The reactive functional group 109 is more preferably a thiol group due to excellent bonding force.

The amino group 111 corresponds to $R_1$ in the general formulae I to V and optionally $R_2$ and $R_3$. The amino group 111 may be a primary, secondary, or tertiary amino group. When the amino group is a secondary or tertiary amino group, it is preferable that the substituent thereof is one or two $C_1$ to $C_{12}$ alkyl groups. When the carbon atoms of the alkyl group are 12 or less, the quaternary nitrogen cation and the amino group are not too far apart, and the effect of improving the reduction efficiency by the amino group can be obtained, as described later. It is more preferably that the carbon atoms of the alkyl group are 2 to 6. The amino group 111 may form a salt with a hydrofluoric acid, a hydrochloric acid, a hydrobromic acid, an iodic acid, a sulfuric acid, a nitric acid, a phosphoric acid, or the like. The modified organic molecule 112 forms a salt with the counter anion represented by X⁻ in the general formulae I to V. Specifically, an ammonium salt, a piperidinium salt, a pyrrolidinium salt, a pyridinium salt, or an imidazolium salt is formed. In FIG. 1, the counter anion is omitted. In FIG. 2, a bromide ion is described as the counter anion.

The counter anion may be, but is not limited to, a fluoride ion, a chloride ion, a bromide ion, an iodide ion, $HCO_3^-$, $BF_4^-$, $PF_6^-$, $CF_3COO^-$, $CF_3SO_3^-$, $NO_3^-$, $SCN^-$, $N(CN)_2^-$, $C(CN)_3^-$ $(CF_3SO_2)_3C^-$, a bis(trifluoromethoxysulfonyl)imide anion, a bis(trifluoromethoxysulfonyl)imide anion, a bis(perfluoroethylsulfonyl)imide anion, or the like.

Examples of the modified organic molecules 112 include the following molecules: 1-(2-mercaptoethyl)-3-aminomethylimidazolium bromide, 1-(3-mercaptopropyl)-3-aminomethylimidazolium bromide, 1-(4-mercaptobutyl)-3-aminomethylimidazolium bromide, 1-(5-mercaptopentyl)-3-aminomethylimidazolium bromide, 1-(6-mercaptohexyl)-3-aminomethylimidazolium bromide, 1-(8-mercaptooctyl)-3-aminomethylimidazolium bromide, 1-(9-mercaptononyl)-3-aminomethylimidazolium bromide, 1-(10-mercaptodecyl)-3-aminomethylimidazolium bromide, 1-(11-mercaptoundecyl)-3-aminomethylimidazolium bromide, 1-(12-mercaptododecyl)-3-aminomethylimidazolium bromide, 1-(2-mercaptoethyl)-3-(2-aminoethyl)imidazolium bromide, 1-(2-mercaptoethyl)-3-(3-aminopropyl)imidazolium bromide, 1-(2-mercaptoethyl)-3-(4-aminobutyl)imidazolium bromide, 1-(2-mercaptoethyl)-3-(5-aminopentyl)imidazolium bromide, 1-(2-mercaptoethyl)-3-(6-aminohexyl)imidazolium bromide, 1-(2-mercaptoethyl)-3-(8-aminooctyl)imidazolium bromide, 1-(2-mercaptoethyl)-3-(9-aminonyl)imidazolium bromide, 1-(2-mercaptoethyl)-3-(10-aminodecyl)imidazolium bromide, 1-(2-mercaptoethyl)-3-(11-aminoundecyl)imidazolium bromide, 1-(2-mercaptoethyl)-3-(12-aminododecyl)imidazolium bromide, 1-(4-mercaptobutyl)-3-(2-methylaminoethyl)imidazolium bromide, 1-(6-mercaptohexyl)-3-(3-dimethylaminopropyl)imidazolium bromide, 1-(8-mercaptohexyl)-3-(4-ethylmethylaminobutyl)imidazolium bromide, 1-(2-mercaptoethyl)-4-aminomethylpyridinium bromide, 1-(3-mercaptopropyl)-4-aminomethylpyridinium bromide, 1-(4-mercaptobutyl)-4-aminomethylpyridinium bromide, 1-(5-mercaptopentyl)-4-aminomethylpyridinium bromide, 1-(6-mercaptohexyl)-4-aminomethylpyridinium bromide, 1-(8-mercaptooctyl)-4-aminomethylpyridinium bromide, 1-(9-mercaptononyl)-4-aminomethylpyridinium bromide, 1-(10-mercaptodecyl)-4-aminomethylpyridinium bromide, 1-(11-mercaptoundecyl)-4-aminomethylpyridinium bromide, 1-(12-mercaptododecyl)-4-aminomethylpyridinium bromide, 1-(2-mercaptoethyl)-4-(2-aminoethyl) pyridinium bromide, 1-(2-mercaptoethyl)-4-(3-aminopropyl)pyridinium bromide, 1-(2-mercaptoethyl)-4-(4-aminobutyl) pyridinium bromide, 1-(2-mercaptoethyl)-4-(5-aminopentyl)pyridinium bromide, 1-(2-mercaptoethyl)-4-(6-aminohexyl)pyridinium bromide, 1-(2-mercaptoethyl)-4-(8-aminooctyl)pyridinium bromide, 1-(2-mercaptoethyl)-4-(9-aminononyl)pyridinium bromide, 1-(2-mercaptoethyl)-4-

(10-aminodecyl)pyridinium bromide, 1-(2-mercaptoethyl)-4-(11-aminoundecyl)pyridinium bromide, 1-(2-mercaptoethyl)-4-(12-aminododecyl)pyridinium bromide, 1-(5-mercaptopentyl)-4-(3-methylaminopropyl) pyridinium bromide, 1-(9-mercaptononyl)-4-(4-dimethylaminobutyl) pyridinium bromide, 1-(11-mercaptoundecyl)-4-(6-ethylmethylaminohexyl)pyridinium bromide, 1-(2-mercaptoethyl)-1-aminomethylpyrrolidinium bromide, 1-(3-mercaptopropyl)-1-aminomethylpyrrolidinium bromide, 1-(4-mercaptobutyl)-1-aminomethylpyrrolidinium bromide, 1-(5-mercaptopentyl)-1-aminomethylpyrrolidinium bromide, 1-(6-mercaptohexyl)-1-aminomethylpyrrolidinium bromide, 1-(8-mercaptooctyl)-1-aminomethylpyrrolidinium bromide, 1-(9-mercaptononyl)-1-aminomethylpyrrolidinium bromide, 1-(10-mercaptodecyl)-1-aminomethylpyrrolidinium bromide, 1-(11-mercaptoundecoyl)-1-aminomethylpyrrolidinium bromide, 1-(12-mercaptododecyl)-1-aminomethylpyrrolidinium bromide, 1-(2-mercaptoethyl)-1-(2-aminoethyl)pyrrolidinium bromide, 1-(2-mercaptoethyl)-1-(3-aminopropyl)pyrrolidinium bromide, 1-(2-mercaptoethyl)-1-(4-aminobutyl)pyrrolidinium bromide, 1-(2-mercaptoethyl)-1-(6-aminohexyl)pyrrolidinium bromide, 1-(2-mercaptoethyl)-1-(8-aminooctyl)pyrrolidinium bromide, 1-(2-mercaptoethyl)-1-(9-aminononyl)pyrrolidinium bromide, 1-(2-mercaptoethyl)-1-(10-aminodecyl)pyrrolidinium bromide, 1-(2-mercaptoethyl)-1-(11-aminoundecyl)pyrrolidinium bromide, 1-(2-mercaptoethyl)-1-(12-aminododecyl)pyrrolidinium bromide, 1-(2-mercaptoethyl)-1-(4-methylaminobutyl)pyrrolidinium bromide, 1-(3-mercaptopropyl)-1-(8-dimethylaminooctyl) pyrrolidinium bromide, 1-(4-mercaptobutyl)-1-(9-ethylmethylaminononyl)pyrrolidinium bromide, 1-(2-mercaptoethyl)-1-aminomethylpiperidinium bromide, 1-(3-mercaptopropyl)-1-aminomethylpiperidinium bromide, 1-(4-mercaptobutyl)-1-aminomethylpiperidinium bromide, 1-(5-mercaptopentyl)-1-aminomethylpiperidinium bromide, 1-(6-mercaptohexyl)-1-aminomethylpiperidinium bromide, 1-(8-mercaptooctyl)-1-aminomethylpiperidinium bromide, 1-(9-mercaptononyl)-1-aminomethylpiperidinium bromide, 1-(10-mercaptodecyl)-1-aminomethylpiperidinium bromide, 1-(11-mercaptoundecyl)-1-aminomethylpiperidinium bromide, 1-(12-mercaptododecyl)-1-aminomethylpiperidinium bromide, 1-(2-mercaptoethyl)-1-(2-aminoethyl)piperidinium bromide, 1-(2-mercaptoethyl)-1-(3-aminopropyl) piperidinium bromide, 1-(2-mercaptoethyl)-1-(4-aminobutyl)piperidinium bromide, 1-(2-mercaptoethyl)-1-(6-aminohexyl)piperidinium bromide, 1-(2-mercaptoethyl)-1-(8-aminooctyl)piperidinium bromide, 1-(2-mercaptoethyl)-1-(9-aminonyl)piperidinium bromide, 1-(2-mercaptoethyl)-1-(10-aminodecyl)piperidinium bromide, 1-(2-mercaptoethyl)-1-(11-aminoundecyl)piperidinium bromide, 1-(2-mercaptoethyl)-1-(12-aminododecyl)piperidinium bromide, 1-(10-mercaptodecyl)-1-(9-methylaminononyl)piperidinium bromide, 1-(11-mercaptoundecyl)-1-(10-dimethylaminodecyl)piperidinium bromide, 1-(12-mercaptododecyl)-1-(12-ethylmethylaminododecyl) piperidinium bromide, 2-mercaptoethyl-(aminomethyl) dimethylammonium bromide, 3-mercaptopropyl-(aminomethyl)dimethylammonium bromide, 4-mercaptobutyl-(aminomethyl)dimethylammonium bromide, 5-mercaptopentyl-(aminomethyl)dimethylammonium bromide, 6-mercaptohexyl-(aminomethyl)dimethylammonium bromide, 8-mercaptooctyl-(aminomethyl)dimethylammonium bromide, 9-mercaptononyl-(aminomethyl)dimethylammonium bromide, 10-mercaptodecyl-(aminomethyl) dimethylammonium bromide, 11-mercaptoundecyl-(aminomethyl)dimethylammonium bromide, 12-mercaptododecyl-(aminomethyl)dimethylammonium bromide, 2-mercaptoethyl-(3-aminopropyl)dimethylammonium bromide, 2-mercaptoethyl-(4-aminobutyl)dimethylammonium bromide, 2-mercaptoethyl-(5-aminopentyl)dimethylammonium bromide, 2-mercaptoethyl-(6-aminohexyl) dimethylammonium bromide, 2-mercaptoethyl-(8-aminooctyl)dimethylammonium bromide, 2-mercaptoethyl-(9-aminonyl)dimethylammonium bromide, 2-mercaptoethyl-(10-aminodecyl)dimethylammonium bromide, 2-mercaptoethyl-(11-aminoundecyl)dimethylammonium bromide, 2-mercaptoethyl-(12-aminododecyl)dimethylammonium bromide, 5-mercaptopentyl-(8-methylaminononyl)ethylmethylammonium bromide, 6-mercaptohexyl-(6-dimethylaminohexyl)methylpropylammonium bromide, and 8-mercaptooctyl-(4-ethylmethylaminobutyl)butylhexylammonium bromide.

Next, a method for producing the reduction catalyst 1 will be described.

First, the metal layer 102 is formed on the surface of the current collector 101. As a method therefor, a known vacuum film formation method such as a sputtering method, a vapor deposition method, an Atomic Layer Deposition (ALD) method, or the like can be used.

Next, the modified organic molecule 112 is fixed to the metal layer 102 by bonding the reactive functional group 109 to the metal layer 102. As a method therefor, a known method can be used. For example, a method of bring the current collector 101 provided with the metal layer 102 into contact with a solution in which the modified organic molecules 112 are dissolved, a method of forming a film on the surface of the current collector 101 by evaporating the modified organic molecules 112 in a high vacuum, a method of spraying the modified organic molecules 112 onto the surface of the current collector 101 by spraying or the like can be used.

In the method using the solution in which the modified organic molecules 112 are dissolved, the modified organic molecules 112 chemically adsorbed on the metal layer 102 forms an aggregate spontaneously by van der Waals force or hydrophobic interaction between adsorbed molecules. Then, the adsorbed molecules are collected densely, whereby a monolayer having uniform alignment is formed.

As the solvent which dissolves the modified organic molecule 112, any solvent capable of dissolving the organic molecules may be used. For example, the solvent can be selected from alcohols, such as ethanol, and aromatic or aliphatic organic solvents, such as toluene and hexane. It is preferable to use ethanol because of high solubility of the modified organic molecules 112 and ease of handling.

An example of a method for fixing the modified organic molecules 112 to the metal layer 102 will be described in more detail.

First, a solution in which the modified organic molecules 112 are dissolved is prepared. Next, the current collector 101 including the metal layer 102 formed thereon is immersed in the prepared solution. The immersion time is several minutes to several hours. Due to this, the modified organic molecules 112 are fixed on the surface of the metal layer 102. Conditions such as a concentration of the modified organic molecules 112, an immersion time, an immersion temperature, and the like can be appropriately changed according to the structure of the modified organic molecule 112, and the like. These conditions affect a formation state of the monolayer including the modified organic molecules 112.

When the concentration of the prepared solution is too low, it takes time to form a monolayer layer. On the other hand, when the concentration is too high, molecules are further adsorbed on the monolayer, and thus, a laminated film may be formed. Therefore, the concentration of the modified organic molecules 112 is preferably 0.1 mM to 100 mM, and more preferably 1 mM to 10 mM.

It is preferable that the immersion time is sufficient to form a dense monolayer with uniform orientation. The immersion time is preferably 1 minute to 100 hours, and more preferably 12 hours to 72 hours.

The temperature of the prepared solution during immersion affects the formation of a dense monolayer with uniform orientation. Therefore, it is desirable that the temperature is room temperature (25° C.) to 60° C., taking into account vapor pressure and boiling point of the solvent.

The fact that the modified organic molecule 112 is fixed on the surface of the metal layer 102 can be confirmed by a known electrochemical method or a known surface analysis method.

As the electrochemical method, a cyclic voltammetry method can be used. Specific examples will be described below. First, 0.2 M potassium chloride (KCl) aqueous solution in which 1 mM potassium hexacyanoferrate (III) ($K_3$[Fe(CN)$_6$]) or 1 mM hexaammine ruthenium (III) chloride ([Ru(NH$_3$)$_6$]Cl$_3$) is dissolved is prepared. In this aqueous solution, electrochemical responses of the current collector 101 before and after a process of adsorbing the modified organic molecule 112 are measured and the results thereof are compared with each other.

As the electrochemical response, a reaction current by an electrochemical redox reaction of hexacyanoferrate (III) anion or hexaammine ruthenium (III) cation is measured. The reaction current for the current collector 101 to which the modified organic molecule 112 is fixed decreases as compared with the reaction current for the current collector 101 to which the modified organic molecule 112 is not fixed. This is due to the inhibition of the redox reaction of the hexacyanoferrate (III) anion or the hexaammine ruthenium (III) cation because the modified organic molecule 112 is fixed to the metal layer 102. Therefore, by measuring the reaction current, it can be indirectly confirmed that the modified organic molecule 112 is fixed.

As the surface analysis method, a Fourier transform infrared spectrophotometer (FT-IR) using a reflection method can be used. According to this method, an infrared spectrum of a thin film and a molecular adsorption species on the surface of the current collector 101 can be measured with high sensitivity. That is, it is possible to know the structure of the organic molecule, in particular, information on the functional group. In addition, X-ray photoelectron spectroscopy (XPS) can be used as the surface analysis method. According to this method, the modified organic molecule 112 and, when the modified organic molecule 112 has an anion, the composition of the anion can be measured. In addition, it is also possible to determine the presence or absence of the modified organic molecule 112 from a difference in wettability of water by using a contact angle meter.

Next, as the reduction reaction in the reduction catalyst 1, the reduction of $CO_2$ will be described as an example. In an elementary reaction of the $CO_2$ reduction reaction, $CO_2$ becomes a $CO_2$ radical anion by one-electron reduction reaction. A large overvoltage is required for this reaction. This overvoltage is a loss of energy and causes a reduction in energy conversion efficiency. In addition, a reduction reaction of water or hydrogen ions occurs as a side reaction together with the $CO_2$ reduction reaction, and hydrogen is generated. The side reaction lowers Faraday efficiency of the $CO_2$ reduction reaction. However, the reduction catalyst 1 according to the present embodiment can achieve high reduction efficiency.

In the reduction catalyst 1, the quaternary nitrogen cation forms a reaction intermediate with $CO_2$. Therefore, it contributes to generation and stabilization of $CO_2$ radical anion. Thus, the reduction catalyst 1 can cause a $CO_2$ reduction reaction with low energy. As a result, the energy conversion efficiency of the reduction catalyst can be improved. In addition, the quaternary nitrogen cation has an effect of inhibiting the access of water and hydrogen ions to the metal layer 102. Therefore, the quaternary nitrogen cation can impart reaction selectivity to the reduction reaction in the metal layer 102. That is, the generation of hydrogen by side reaction can be suppressed, and Faraday efficiency can be improved.

In addition, the amino group of the modified organic molecule 112 reacts with the $CO_2$ molecule to form a carbonate. Therefore, $CO_2$ molecules necessary for the reduction reaction can be attracted and supplied to the quaternary nitrogen cations or the metal layer 102. In addition, the amino group forms a salt with a carboxylic acid (for example, a formic acid, an acetic acid, an oxalic acid, or the like) generated by $CO_2$ reduction. Therefore, this has the effect of promoting multi-electron reduction reaction in which reduction occurs continuously. As a result, the reduction efficiency can be improved.

From the above, according to the present embodiment, it is possible to provide a reduction catalyst with high reaction efficiency.

In the reduction catalyst 1 according to the present embodiment, a raw material selected from the group consisting of carbon dioxide, an oxalic acid, a glycolic acid, and a glycolaldehyde can be used as a reducing raw material. A reduction product is changed by the interaction between the quaternary nitrogen cation, the metal layer 102, and the reducing raw material. For example, when $CO_2$ is used as the raw material, carbon monoxide (CO), a formic acid (HCOOH), formaldehyde (HCHO), methanol (CH$_3$OH), an acetic acid (CH$_3$COOH), acetaldehyde (CH$_3$CHO), ethanol (CH$_3$CH$_2$OH), an oxalic acid ((COOH)$_2$), a glycolic acid (C$_2$H$_2$O$_3$), glycol aldehyde (C$_2$H$_2$O$_2$), and ethylene glycol (HOCH$_2$CH$_2$OH) may be generated.

However, the reduction catalyst 1 according to the present embodiment can produce ethylene glycol with high selectivity. Therefore, the use of the reduction catalyst 1 can provide a method of using a reduction catalyst to reduce a raw material selected from the group consisting of carbon dioxide, an oxalic acid, a glycolic acid, and a glycol aldehyde to generate a product including ethylene glycol.

<Second Embodiment>

Next, a reduction catalyst according to a second embodiment will be described with reference to FIGS. 3 and 4. In the drawings, the same reference numerals are assigned to the same parts as in the first embodiment. In addition, redundant descriptions are given as necessary.

Figure 3:
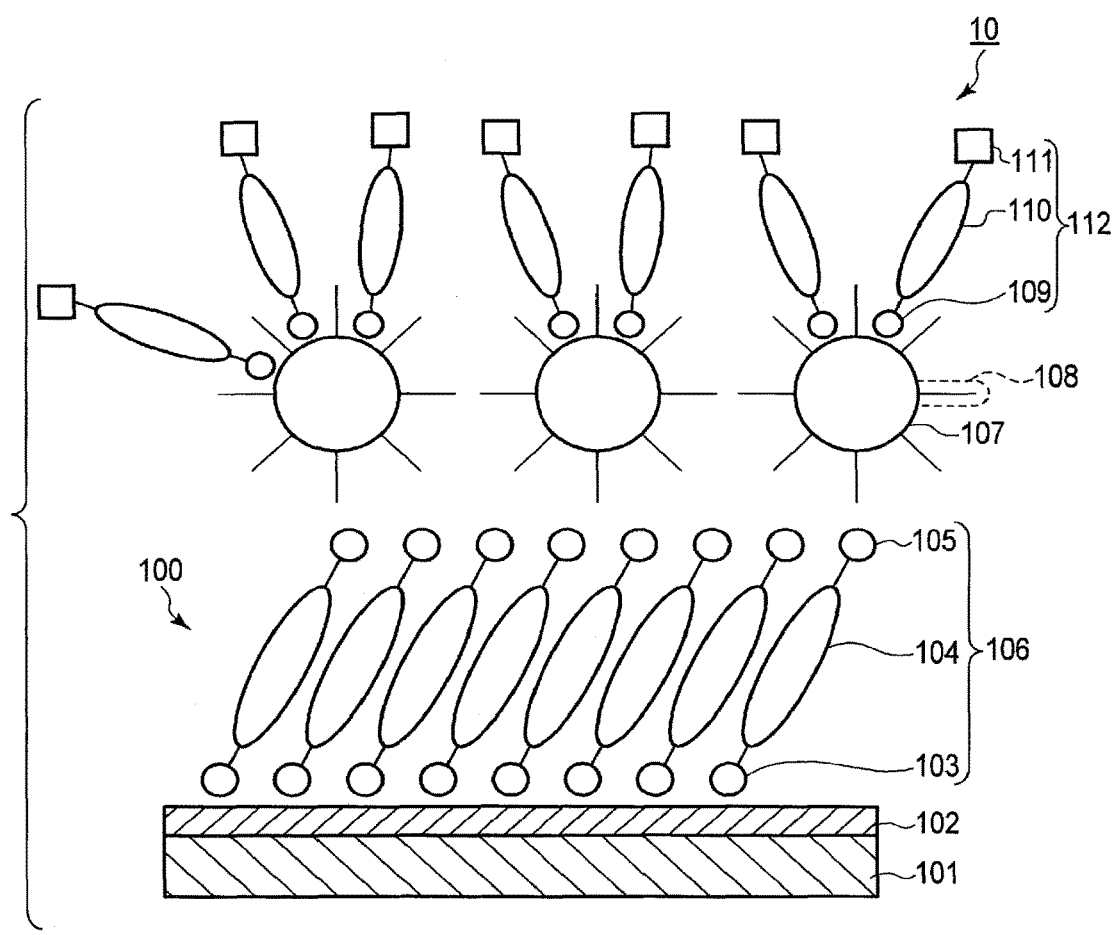
FIG. 3 is a view showing a structure of a reduction catalyst according to a second embodiment.
Figure 4:
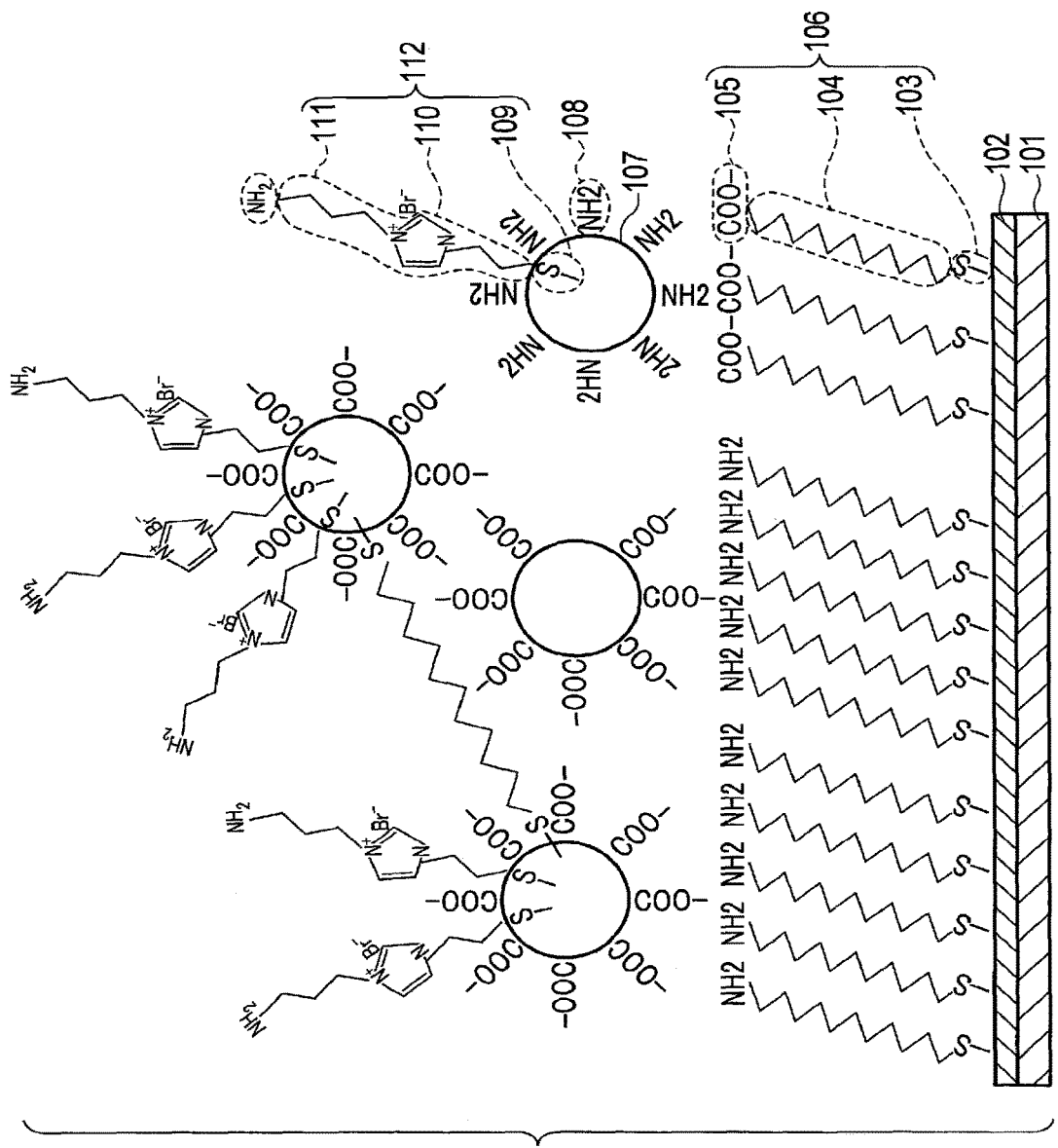
FIG. 4 is a view showing an example of the structure of the reduction catalyst of FIG. 3 in detail.

FIG. 3 is a view showing a structure of a reduction catalyst 10 according to the present embodiment, and FIG. 4 is a view showing an example of the structure of the reduction catalyst 10 in detail. As shown in FIG. 3, the reduction catalyst 10 includes a current collector 101 including a metal layer 102, a spacer organic molecular layer 100 formed on the metal layer 102, metal fine particles 107 bonded to the spacer organic molecular layer 100, and organic molecules 112 including quaternary nitrogen cations bonded to the metal fine particles 107.

As the current collector 101 and the metal layer 102, those similar to those in the first embodiment can be used.

The spacer organic molecular layer 100 is a monolayer (Self-Assembled Monolayer) formed by chemical adsorption of the spacer organic molecules 106 on the surface of the metal layer 102 and self-assembling.

The spacer organic molecule 106 has a skeleton 104 including a quaternary nitrogen cation, a first reactive functional group 103 located at one end, and a second reactive functional group 105 located at the other end. The quaternary nitrogen cation is preferably at least one cation selected from an alkylammonium cation, a pyridinium cation, a piperidinium cation, a pyrrolidinium cation, and an imidazolium cation.

As a chain length of the spacer organic molecule 106 becomes longer, a denser and aligned molecular layer is formed on the metal layer 102. Therefore, by increasing the chain length, the metal fine particles 107 are easily fixed, and a molecular layer having high durability can be formed. On the other hand, when the chain length is too long, a resistance of a tunnel current in the spacer organic molecular layer 100 increases, so that an electrode resistance of the reduction catalyst 10 increases. Therefore, a total number of carbon atoms included in the spacer organic molecules 106 is preferably in a range of 2 to 12, and more preferably in a range of 2 to 6.

The first reactive functional group 103 has an affinity for the metal layer 102 and chemically reacts with the metal layer 102 to bond thereto. Due to this, the spacer organic molecule 106 is fixed to the metal layer 102. The first reactive functional group 103 is preferably a functional group which can be covalently bonded to the metal layer 102, and is preferably selected from, for example, a thiol group, a disulfide group, and a thiocyanate group. The first reactive functional group 103 is more preferably a thiol group due to excellent bonding force.

The second reactive functional group 105 has an affinity for the metal fine particles 107 and chemically reacts with the metal fine particles 107 to bond thereto. Due to this, the metal fine particles 107 are fixed to the surface of the spacer organic molecular layer 100. The second reactive functional group 105 is preferably a functional group which can be electrostatically bonded to the charged metal fine particles 107, and is preferably selected from, for example, an amino group and a carboxyl group. Alternatively, the second reactive functional group 105 is preferably a functional group which can be covalently bonded to the metal fine particles 107, and is preferably selected from functional groups such as a thiol group, a disulfide group, a thiocyanate group, and the like.

Examples of the spacer organic molecule 106 include molecules similar to those in the examples of the modified organic molecule 112 described in the first embodiment. Further, examples of the spacer organic molecule 106 include the following molecules: 10-carboxy-1-decanethiol, 7-carboxy-1-heptanethiol, 5-carboxy-1-pentanethiol, 3-carboxy-1-propanethiol, a mercaptoacetic acid, 10-carboxydecyl-disulfide, 7-carboxyheptyl-disulfide, 5-carboxypentyl-disulfide, a 4,4'-dithiodibutanoic acid, 11-amino-1-undecanethiol, 8-amino-1-octanethiol, 6-amino-1-hexanethiol, 11-mercaptoundecane-1-trimethylammonium chloride, sodium 11-mercaptoundecane-1-sulfonate, 11-mercaptoundecane-1-phosphone, 1,2-ethanedithiol, 1,3-propanedithiol, 1,4-butanedithiol, 1,5-pentanedithiol, 1,6-hexanedithiol, 1,7-heptanedithiol, 1,8-octanedithiol, 1,9-nonanedithiol, 1,10-decanedithiol, 1,11-undecanedithiol, 1,12-dodecanedithiol, 1,13-tridecanedithiol, 1,14-tetradecanedithiol, 1,15-pentadecanedithiol, and a 1,16-hexadecanedithiolic acid.

The metal fine particle 107 functions as a catalyst which activates the reduction reaction. At least one element selected from the group consisting of Au, Ag, Cu, Pt, Zn, Fe, Ti, Sn, In, Bi, and Ni is used as a material of the metal fine particle. Since the catalyst activity is particularly high, metal fine particles including Au or Ag are preferably used as the metal fine particles 107.

An average grain size of the metal fine particles 107 is preferably 1 nm to 300 nm. When the average grain size is 300 nm or less, the activity efficiency of the catalyst can be increased. In addition, it is difficult to produce metal fine particles 107 having an average grain size of less than 1 nm. When the average grain size of the metal fine particles 107 is 150 nm or less, it is more preferable because the activity efficiency of the catalyst is further improved. Note that the metal fine particles 107 may be primary particles having an average grain size of 50 nm or less, but secondary particles obtained by aggregating such primary particles may also be used.

The average grain size of the metal fine particles 107 can be measured through grain size distribution measurement by a dynamic light scattering method. Specifically, a solution in which the metal fine particles 107 are dispersed is irradiated with laser light to detect fluctuation of scattered light to which diffusion coefficient is reflected. From the result, it is possible to calculate a particle diameter by using the Stokes-Einstein equation. In a frequency distribution in which an appearance ratio for each particle size is determined, a largest particle diameter or a maximum value of the distribution is a mode diameter, which is taken as an average particle diameter.

The metal fine particles have organic molecules 108 having charges on a part of the surface thereof. Due to this, the surface of the metal fine particle 107 is charged. The metal fine particles 107 are immobilized on the surface of the spacer organic molecular layer 100 by an electrostatic attraction (electrostatic bonding) between the charge on the surface of the metal fine particle 107 and the charge of the second reactive functional group 105. The charge of the organic molecule 108 may be either a positive charge or a negative charge.

When the charge of the organic molecule 108 is a negative charge, the surface of the metal fine particle 107 also has a negative charge. In this case, the metal fine particles 107 can be immobilized by using the spacer organic molecules 106 including an amino group as the second reactive functional group 105.

On the other hand, when the charge of the organic molecule 108 is a positive charge, the metal fine particle 107 can be immobilized by using the spacer organic molecule 106 including a carboxyl group as the second reactive functional group 105.

When the metal fine particles 107 have charges, electrostatic repulsive force is generated between the particles, and thus, it is possible to prevent nanoparticle-sized fine particles from being aggregated to coarsen each other.

The organic molecule 112 including a quaternary nitrogen cation is bonded to the metal fine particle 107 and has a function of promoting a reduction reaction. As the organic molecule 112 including the quaternary nitrogen cation, the same as in the first embodiment can be used. Here, the organic molecule including the quaternary nitrogen cation is referred to as a modified organic molecule. The reactive functional group 109 of the modified organic molecule 112 has an affinity for the metal fine particle 107 and is chemically bonded to the metal fine particle 107. Due to this, the modified organic molecule 112 is fixed to the metal fine particle 107.

Next, a method for producing the reduction catalyst 10 will be described.

First, the metal layer 102 is formed on the surface of the current collector 101. As a method therefor, a known vacuum film formation method such as a sputtering method, a vapor deposition method, an Atomic Layer Deposition (ALD) method, or the like can be used.

Next, the spacer organic molecules 106 are fixed to the metal layer 102, and the spacer organic molecular layer 100 is formed. As a method therefor, in the method for producing the reduction catalyst 1 according to the first embodiment, the same method as the method for fixing the modified organic molecules 112 to the metal layer 102 can be used.

The formation of the spacer organic molecular layer 100 on the surface of the metal layer 102 can be confirmed by the same method as the method of confirming whether the modified organic molecules 112 are fixed to the metal layer 102 in the method for producing the reduction catalyst 1 according to the first embodiment. Next, the metal fine particles 107 are prepared. The charged organic molecules 108 are fixed to the metal fine particles. As a method therefor, there are the following first method and second method.

(First Method)

In the method for preparing metal fine particles, a reducing agent such as a citric acid is used when metal fine particles are reduced and precipitated from a solution layer. Due to this, the citric acid is imparted to the surface of the metal fine particle. As a result, the surfaces of the metal fine particles are negatively charged. Then, molecules including an amino group are electrostatically bonded to the surfaces of the negatively charged metal fine particles.

(Second Method)

Amine molecules including a covalent reactive group such as thiol are bonded to the surfaces of uncharged metal fine particles. Thus, the metal fine particles are positively charged. According to this method, it is possible to fix the charged organic molecules 108 regardless of the presence or absence of charge on the surface of the metal fine particle and whether the charge is positive or negative.

Next, the metal fine particles 107, to which the charged organic molecules 108 are fixed, are fixed to the surface of the spacer organic molecular layer 100. Specifically, the metal fine particles 107 are dispersed in an aqueous solution to prepare a dispersion liquid. The current collector 101, on which the spacer organic molecular layer 100 is formed, is immersed in the dispersion liquid. Due to this, the second reactive functional group 105 of the spacer organic molecular layer 100 and the organic molecule 108 on the surface of the metal fine particle 107 are electrostatically bonded, and the metal fine particle 107 is fixed to the spacer organic molecular layer 100.

The solution in which the metal fine particles 107 are dispersed is not particularly limited as long as the metal fine particles 107 can be stably dispersed. For example, water, ethanol, toluene, or the like can be used. Due to ease of handling, water or ethanol is preferably used.

Conditions such as a concentration of the dispersion liquid, an immersion time, an immersion temperature, and the like are appropriately changed because the conditions depend on the synthesis method and stability of the metal fine particles 107.

When the concentration of the dispersion liquid is too low, it takes time to fix the metal fine particles 107. On the other hand, when the concentration is too high, the metal fine particles 107 may aggregate in the dispersion liquid and may not be fixed to the spacer organic molecular layer 100. Therefore, the concentration of the metal fine particles in the dispersion liquid is preferably 0.01 mM to 10 mM, and more preferably 0.1 mM to 1 mM.

The immersion time is preferably 1 hour to 50 hours, and more preferably 5 hours to 24 hours, so as to fix a sufficient amount of the metal fine particles 107.

The temperature of the dispersion liquid during immersion is preferably room temperature (25° C.) to 35° C. When the temperature is too high, the dispersion stability of the metal fine particles 107 is reduced, and thus, the metal fine particles 107 may aggregate.

The fact that the metal fine particles 107 are fixed on the surface of the spacer organic molecular layer 100 can be confirmed by a known electrochemical method or a known surface analysis method.

As the electrochemical method, a cyclic voltammetry method can be used. Specific examples will be described below. First, 0.2 M potassium chloride (KCl) aqueous solution in which 1 mM potassium hexacyanoferrate (III) ($K_3$[Fe(CN)$_6$]) or 1 mM hexaammine ruthenium (III) chloride ([Ru(NH$_3$)$_6$]Cl$_3$) is dissolved is prepared. In this aqueous solution, electrochemical responses of the current collector 101 before and after a process of fixing the metal fine particles 107 are measured and the results thereof are compared with each other.

As the electrochemical response, a reaction current by electrochemical redox reaction of hexacyanoferrate (III) anion or hexaammine ruthenium (III) cation is measured. The reaction current for the current collector 101 to which the metal fine particles 107 are fixed increases as compared with the reaction current for the current collector 101 to which the metal fine particles 107 are not fixed. This is due to the redox reaction of the hexacyanoferrate (III) anion or the hexaammine ruthenium (III) cation because the metal fine particles 107 are fixed to the spacer organic molecular layer 100. Therefore, by measuring the reaction current, it can be indirectly confirmed that the metal fine particles 107 are fixed.

As the surface analysis method, it can be directly observed by a scanning electron microscope (SEM), a transmission electron microscope (TEM), an atomic force microscope (AFM), or a scanning transmission electron microscope (STEM). In addition, the composition of the metal can be evaluated by energy dispersive X-ray analysis (EDX), electron beam microanalyzer (EPMA), X-ray photoelectron spectroscopy (XPS), or the like.

Next, the modified organic molecules 112 are fixed to the metal fine particles 107 fixed to the spacer organic molecular layer 100. As the method therefor, in the method for producing the reduction catalyst 1 according to the first embodiment, the same method as the method for fixing the modified organic molecules 112 to the metal layer 102 can be used.

An example of a method for fixing the modified organic molecules 112 to the metal fine particles 107 will be described in more detail.

First, a solution in which the modified organic molecules 112 are dissolved is prepared. Next, the current collector 101 including the metal fine particles 107 formed thereon is immersed in the prepared solution. The immersion time is several minutes to several hours. Due to this, the modified organic molecules 112 are fixed on the surfaces of the metal fine particles 107. Conditions such as a concentration of the modified organic molecules 112, an immersion time, an immersion temperature, and the like can be appropriately changed according to the structure of the modified organic molecule 112, and the like.

When the concentration of the prepared solution is too low, it takes time to fix a sufficient amount of the modified organic molecules 112. On the other hand, when the concentration is too high, excessive modified organic molecules 112 are adsorbed, and thus, molecules may be laminated. Therefore, the concentration of the modified organic molecules 112 is preferably 0.1 mM to 100 mM, and more preferably 1 mM to 10 mM.

It is preferable that the immersion time is sufficient to form a dense monolayer with uniform orientation. The immersion time is preferably 1 minute to 100 hours, and more preferably 12 hours to 72 hours.

The temperature of the prepared solution during immersion affects the formation of a dense monolayer with uniform orientation. Therefore, it is desirable that the temperature is room temperature (25° C.) to 60° C., taking into account vapor pressure and boiling point of the solvent.

The reduction catalyst 10 can be produced by the method described above.

In addition, it is also possible to further laminate the fine metal particles 107 on the modified organic molecules 112. An example of the method for further laminating the modified organic molecules 112 and the metal fine particles 107 will be described below in more detail.

The quaternary nitrogen cation included in the modified organic molecule 112 has a positive charge. Therefore, when the modified organic molecule 112 is brought into contact with an aqueous solution in which the anion including the metal element constituting the metal fine particle 107 is dissolved, the quaternary nitrogen cation and the anion including the metal element are electrostatically bonded to each other by an anion exchange reaction. Then, metal nanoparticles can be supported on the surface of the quaternary nitrogen cation by electrochemical reduction or reduction with a hydrogen gas in the aqueous solution. These metal nanoparticles correspond to the metal fine particles 107.

Au or Pt can be used as the metal element which can be precipitated in the vicinity of the quaternary nitrogen cation. As a raw material of the anion including Au or Pt, a salt such as sodium tetrachloroaurate (III) dihydrate ($Na[AuCl_4]$ $2H_2O$), potassium gold (III) chloride ($K[AuCl_4]$), potassium tetrachloroplatinate (II) ($K_2[PtCl_4]$), potassium hexachloroplatinate (IV) ($K_2[PtCl_6]$), or the like can be used.

This method will be described in more detail. First, anion exchange is performed by immersing the current collector 101, fixed to the metal fine particles 107 where the modified organic molecules 112 are fixed, in a solution in which an anion including Au or Pt is dissolved. Due to this, the anion including Au or Pt is electrostatically bonded to the quaternary nitrogen cation included in the modified organic molecule 112. The concentration of the salt of the anion including Au or Pt in the solution in which the anion is dissolved is preferably 0.1 mM to 100 mM. An anion exchange time is preferably 30 minutes to 2 hours.

Subsequently, the current collector 101 after the anion exchange is immersed in an alkaline aqueous solution, and reduction is performed by constant potential reduction electrolysis. As the alkaline aqueous solution, an aqueous solution of sodium hydrogencarbonate having a concentration of 0.5 M can be used. The electrolysis is performed in a condition that a three-electrode cell using the current collector 101 as a working electrode, silver/silver chloride as a reference electrode, and Pt as a counter electrode is used, and a potential of −0.5 V is applied to the working electrode for about 1 hour.

Alternatively, the current collector 101 after the anion exchange is immersed in an aqueous solution, in which $H_2$ gas is dissolved, and is reduced. The immersion may be performed for about 1 hour. Due to this, the metal fine particle 107 can be formed on the surface of the quaternary nitrogen cation.

Next, the modified organic molecule 112 including the quaternary nitrogen cation is further fixed on the surface of the Au or Pt nanoparticle precipitated in the vicinity of the quaternary nitrogen cation. In this way, by repeating the process of precipitating the metal fine particle 107 in the vicinity of the quaternary nitrogen cation and the process of fixing the modified organic molecule 112, the amount of the metal fine particles 107 can be increased.

Next, as the reduction reaction in the reduction catalyst 10, the reduction of $CO_2$ will be described as an example. As described in the first embodiment, the elementary reaction of the ordinary $CO_2$ reduction reaction has a problem that Faraday efficiency is low. However, the reduction catalyst 10 according to the present embodiment can achieve high reduction efficiency.

In the reduction catalyst 10, the reduction reaction occurs in the metal fine particles 107. The quaternary nitrogen cation included in the modified organic molecule 112 forms is a reaction intermediate with $CO_2$. Therefore, it contributes to generation and stabilization of $CO_2$ radical anion. Thus, the reduction catalyst 10 can cause a $CO_2$ reduction reaction with low energy. As a result, the energy conversion efficiency of the reduction catalyst can be improved. In addition, the quaternary nitrogen cation has an effect of inhibiting the access of water and hydrogen ions to the metal fine particles 107. Therefore, the quaternary nitrogen cation can impart reaction selectivity to the reduction reaction in the metal fine particles 107. That is, the generation of hydrogen by side reaction can be suppressed, and Faraday efficiency can be improved.

In addition, the amino group of the modified organic molecule 112 reacts with the $CO_2$ molecule to form a carbonate. Therefore, $CO_2$ molecules necessary for the reduction reaction can be attracted and supplied to the quaternary nitrogen cations or the metal fine particles 107. In addition, the amino group forms a salt with a carboxylic acid (for example, a formic acid, an acetic acid, an oxalic acid, or the like) generated by $CO_2$ reduction. Therefore, this has the effect of promoting multi-electron reduction reaction in which reduction occurs continuously. As a result, the reduction efficiency can be improved.

In addition, since the reduction catalyst 10 has the metal fine particles 107, the reduction catalyst 10 can have a reaction area (surface area) larger than that of the flat metal layer. As a result, the reduction reaction efficiency can be increased.

From the above, according to the present embodiment, it is possible to provide a reduction catalyst with high reaction efficiency.

In the reduction catalyst 10 according to the present embodiment, a raw material selected from the group consisting of carbon dioxide, an oxalic acid, a glycolic acid, and a glycolaldehyde can be used as a reducing raw material. A reduction product is changed by the interaction between the quaternary nitrogen cation, the metal layer 102, and the reducing raw material. For example, when $CO_2$ is used as the raw material, carbon monoxide (CO), a formic acid (HCOOH), formaldehyde (HCHO), methanol ($CH_3OH$), an acetic acid ($CH_3COOH$), acetaldehyde ($CH_3CHO$), ethanol ($CH_3CH_2OH$), an oxalic acid (($COOH)_2$), a glycolic acid ($C_2H_2O_3$), glycol aldehyde ($C_2H_2O_2$), and ethylene glycol ($HOCH_2CH_2OH$) may be generated.

However, the reduction catalyst 10 according to the present embodiment can produce ethylene glycol with high selectivity. Therefore, the use of the reduction catalyst 10 can provide a method of using a reduction catalyst to reduce a raw material selected from the group consisting of carbon dioxide, an oxalic acid, a glycolic acid, and a glycol aldehyde to generate a product including ethylene glycol.

<Third Embodiment>

In the third embodiment, a chemical reactor using the reduction catalyst according to the first embodiment will be described. Although not described, it is also possible to use the reduction catalyst according to the second embodiment instead of the reduction catalyst according to the first embodiment.

First, a photochemical reaction cell provided in a chemical reactor will be described with reference to FIGS. 5 to 7. The photochemical reaction cell includes an oxidation catalyst layer, a reduction catalyst layer including a reduction catalyst, and a power supply element connected to the oxidation catalyst layer and the reduction catalyst layer. It is preferable that the power supply element includes a semiconductor layer that performs charge separation by light energy and can use, for example, a solar cell. The semiconductor layer is preferably disposed between the oxidation catalyst layer and the reduction catalyst layer.

Figure 5:
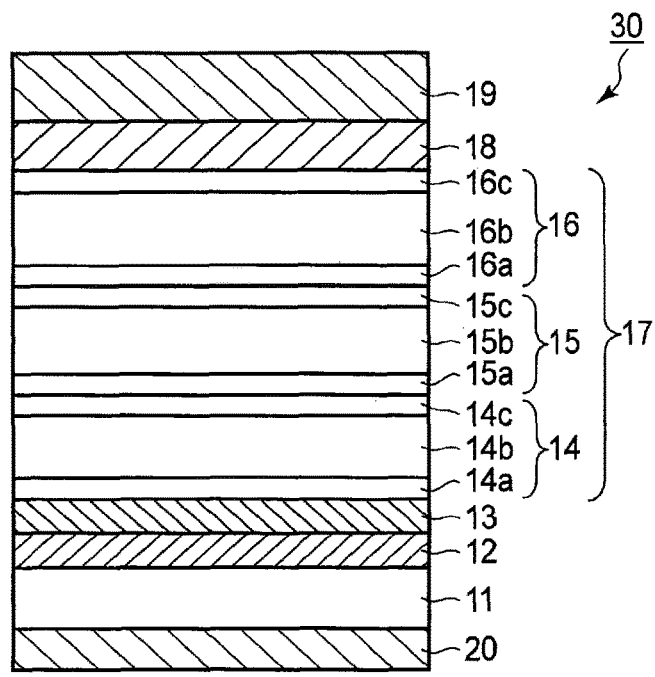
FIG. 5 is a cross-sectional view showing a photochemical reaction cell in a third embodiment.

FIG. 5 is a cross-sectional view showing a photochemical reaction cell 30. As shown in FIG. 5, the photochemical reaction cell 30 is a laminate in which a reduction catalyst layer 20, a substrate 11, a reflective layer 12, a reduction electrode layer 13, a multijunction solar cell 17, an oxidation electrode layer 18, and an oxidation catalyst layer 19 are laminated in this order. In the photochemical reaction cell 30, a side of the reduction catalyst layer 20 is a back side, and a side of the oxidation catalyst layer 19 is a front surface on which light is incident.

The substrate 11 is provided for supporting the photochemical reaction cell and increasing mechanical strength thereof. The substrate 11 includes a material having conductivity. For example, the substrate 11 can include a metal plate including a metal selected from the group consisting of Au, Ag, Cu, Pt, Zn, Fe, Ti, Sn, In, Bi, and Ni, or an alloy plate including at least one of these metals. As the alloy plate, for example, an alloy plate such as SUS can be used. Alternatively, the substrate 11 can include a resin having conductivity, or the like. In addition, the substrate 11 can include a semiconductor substrate such as Si or Ge. In addition, the substrate 11 can also include an ion exchange membrane.

The reflective layer 12 is formed on the surface of the substrate 11. The reflective layer 12 includes a material which can reflect light. For example, the reflective layer 12 can include a metal layer or a distributed Bragg reflective layer including a semiconductor multilayer film. The reflective layer 12 is disposed between the substrate 11 and the multijunction solar cell 17. Therefore, it is possible to reflect the light which is not absorbed by the multijunction solar cell 17 and make the light enter the multijunction solar cell 17 again. Due to this, it is possible to improve the light absorption rate in the multijunction solar cell 17.

The reduction electrode layer 13 is disposed on the reflective layer 12 and is interposed between the reflective layer 12 and an n-type semiconductor layer (an n-type amorphous silicon layer 14a described below) of the multijunction solar cell 17. Therefore, the reduction electrode layer 13 preferably includes a material capable of ohmic contact with the n-type semiconductor layer. The reduction electrode layer 13 includes, for example, a metal such as Ag, Au, Al, or Cu, or an alloy including at least one of them. Alternatively, the reduction electrode layer 13 may include a transparent conductive oxide such as indium tin oxide (ITO), zinc oxide (ZnO), fluorine doped tin oxide (FTO), aluminum doped zinc oxide (AZO), or antimony doped tin oxide (ATO). In addition, the reduction electrode layer 13 may have, for example, a structure in which a metal and a transparent conductive oxide are laminated, a structure in which a metal and other conductive material are combined, or a structure in which a transparent conductive oxide and other conductive material are combined.

The multijunction solar cell 17 is disposed on the reduction electrode layer 13. A first solar cell 14, a second solar cell 15, and a third solar cell 16 are laminated in this order from the reduction electrode layer 13 side. These are solar cells using pin junction semiconductors. Each of the first solar cell 14, the second solar cell 15, and the third solar cell 16 has a different light absorption wavelength. By laminating these in a planar manner, the multijunction solar cell 17 can absorb light of a wide wavelength of sunlight. Therefore, it is possible to utilize solar energy more efficiently. In addition, since the respective solar cells are connected in series, a high open circuit voltage can be obtained.

The first solar cell 14 includes an n-type amorphous silicon (a-Si) layer 14a, an intrinsic amorphous silicon germanium (a-SiGe) layer 14b, and a p-type microcrystalline silicon (μc-Si) layer 14c in this order from the reduction electrode layer 13 side. The a-SiGe layer 14b is a layer which absorbs light in a short wavelength region of about 400 nm. Therefore, in the first solar cell 14, charge separation occurs due to the light energy in the short wavelength region.

The second solar cell 15 includes an n-type a-Si layer 15a, an intrinsic a-SiGe layer 15b, and a p-type μc-Si layer 15c in this order from the reduction electrode layer side. The a-SiGe layer 15b is a layer which absorbs light in an intermediate wavelength region of about 600 nm. Therefore, in the second solar cell 15, charge separation occurs due to the light energy in the intermediate wavelength region.

In addition, the third solar cell 16 includes an n-type a-Si layer 16a, an intrinsic a-Si layer 16b, and a p-type μc-Si layer 16c in this order from the reduction electrode layer 13 side. The a-Si layer 16b is a layer which absorbs light in a long wavelength region of about 700 nm. Therefore, in the third solar cell 16, charge separation occurs due to the light energy in the long wavelength region.

In the multijunction solar cell 17, charge separation occurs due to light in each wavelength region. That is, holes are separated on the positive electrode side (front surface side) and electrons are separated on the negative electrode side (back surface side). Due to this, an electromotive force is generated in the multijunction solar cell 17.

Here, the multijunction solar cell 17 having the laminated structure of three solar cells has been described as an example, but the present invention is not limited thereto. A multijunction solar cell having a laminated structure of two, four, or more solar cells can also be used. Alternatively, instead of the multijunction solar cell 17, a solar cell may be used. In addition, although the solar cell using the pin junction semiconductor has been described, a solar cell using a pn junction semiconductor may be used. In addition, a semiconductor layer including, for example, GaAs, GaInP, AlGaInP, CdTe, CuInGaSe, or the like may be used. Furthermore, various forms such as a single crystal, a poly crystal, and an amorphous state can be applied as the semiconductor layer.

The oxidation electrode layer 18 is disposed on the multijunction solar cell 17, and is interposed between the p-type semiconductor layer of the multijunction solar cell 17 and the oxidation catalyst layer 19. The oxidation electrode layer 18 preferably includes a transparent material capable of ohmic contact with the p-type semiconductor layer. The oxidation electrode layer 18 may include a transparent conductive oxide such as indium tin oxide (ITO), zinc oxide (ZnO), fluorine doped tin oxide (FTO), aluminum doped zinc oxide (AZO), or antimony doped tin oxide (ATO). In addition, the oxidation electrode layer 18 may have, for example, a structure in which a metal and a transparent conductive oxide are laminated, a structure in which a metal and other conductive material are combined, or a structure in which a transparent conductive oxide and other conductive material are combined.

The oxidation catalyst layer 19 is disposed on the positive electrode side of the multijunction solar cell 17 and is formed on the oxidation electrode layer 18. When a hydrogen ion concentration of an electrolytic solution is lower than 7 (pH<7), the oxidation catalyst layer 19 oxidizes $H_2O$ to produce $O_2$ and $H^+$. On the other hand, when the hydrogen ion concentration of the electrolytic solution is larger than 7 (pH>7), the oxidation catalyst layer 19 oxidizes $OH^-$ to produce $O_2$ and $H_2O$. Therefore, the oxidation catalyst layer 19 includes a material which reduces the activation energy for the oxidation reaction. In other words, the oxidation catalyst layer 19 includes a material which reduces the overvoltage when performing a reaction of oxidizing $H_2O$ or $OH^-$ to extract electrons.

As such a material, there are binary metal oxide such as manganese oxide (Mn—O), iridium oxide (Ir—O), nickel oxide (Ni—O), cobalt oxide (Co—O), iron oxide (Fe—O), tin oxide (Sn—O), indium oxide (In—O), or ruthenium oxide (Ru—O), ternary metal oxide such as Ni—Co—O, La—Co—O, Ni—La—O, or Sr—Fe—O, quaternary metal oxide such as Pb—Ru—Ir—O or La—Sr—Co—O, and a metal complex such as a Ru complex or a Fe complex.

The shape of the oxidation catalyst layer 19 is not limited to a thin film shape, and may be a grid shape, a particle shape, or a wire shape.

In the photochemical reaction cell 30, irradiation light passes through the oxidation catalyst layer 19 and the oxidation electrode layer 18 and reaches the multijunction solar cell 17. Therefore, the oxidation electrode layer 18 and the oxidation catalyst layer 19 disposed on the light irradiation surface side are optically transparent to the irradiation light. More specifically, the permeability of the oxidation electrode layer 18 and the oxidation catalyst layer 19 on the irradiation surface side is at least 10% or more, more preferably 30% or more of the irradiation amount of the irradiation light.

The reduction catalyst layer 20 is disposed on the negative electrode side of the multijunction solar cell 17 and is formed on the back surface of the substrate 11. The reduction catalyst layer 20 reduces the reducing raw material such as $CO_2$ to produce a carbon compound (for example, carbon monoxide, a formic acid, formaldehyde, methane, methanol, an acetic acid, acetaldehyde, ethanol, ethylene glycol, or the like). Therefore, the reduction catalyst layer 20 includes a material which reduces the activation energy for reducing the reducing raw material.

As the reduction catalyst layer 20, the reduction catalyst 1 according to the first embodiment is applied. That is, the reduction catalyst layer 20 includes a current collector 101 and an organic molecule 112 including a quaternary nitrogen cation. The current collector 101 may be used as the substrate 11.

In addition, a protective layer having conductivity may be disposed on the surface of the multijunction solar cell 17 or between the electrode layer and the catalyst layer on the light irradiation surface side (between the oxidation electrode layer 18 and the oxidation catalyst layer 19 in the photochemical reaction cell 30). The protective layer prevents corrosion of the multijunction solar cell 17 in the redox reaction. As a result, the lifetime of the multijunction solar cell 17 can be prolonged. In addition, the protective layer has optical transparency as necessary. Examples of the protective layer may include a dielectric thin film such as $TiO_2$, $ZrO_2$ $Al_2O_3$, $SiO_2$, $HfO_2$, and the like. In addition, a film thickness of the protective layer is preferably 10 nm or less, and more preferably 5 nm or less, so as to obtain conductivity by a tunneling effect.

Figure 6:
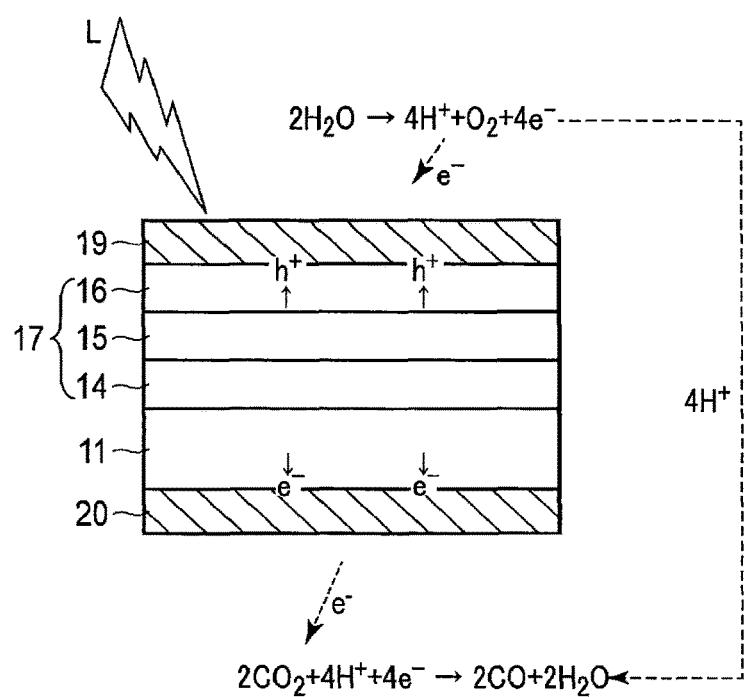
FIG. 6 is a cross-sectional view showing an example of an operation principle of the photochemical reaction cell of FIG. 5.

FIGS. 6 and 7 are cross-sectional views for describing the operation principle of the photochemical reaction cell 30. Here, the reflective layer 12, the reduction electrode layer 13, and the oxidation electrode layer 18 are omitted.

As shown in FIGS. 6 and 7, when light (L) enters from the surface side (the oxidation electrode layer 18 side), the incident light passes through the oxidation catalyst layer 19 (and the oxidation electrode layer 18), and reaches the multijunction solar cell 17. When the multijunction solar cell 17 absorbs light, photoexcited electrons and holes to be paired therewith are generated and separated therefrom. Specifically, in the respective solar cells (the first solar cell 14, the second solar cell 15, and the third solar cell 16), photoexcited electrons move to the n-type semiconductor layer side (the reduction catalyst layer 20 side), and holes generated as a pair of photoexcited electrons move to the p-type semiconductor layer side (oxidation catalyst layer 19 side). That is, charge separation occurs. Due to this, an electromotive force is generated in the multijunction solar cell 17.

The photoexcited electrons generated in the multijunction solar cell 17 are used for the reduction reaction in the reduction catalyst layer 20 which is a negative electrode. The holes are used for the oxidation reaction in the oxidation catalyst layer 19 which is the positive electrode.

An example of a case in which the hydrogen ion concentration of the electrolytic solution is smaller than 7 is shown in FIG. 6. In the vicinity of the oxidation catalyst layer 19, a reaction of the following formula (1) occurs. That is, $H_2O$ is oxidized to generate $O_2$, $H^+$, and electrons. Here, the generated $H^+$ moves to the reduction catalyst layer 20 side via an ion transfer path described below. In the vicinity of the reduction catalyst layer 20, a reaction of the following formula (2) occurs. That is, $CO_2$ is reduced by moved $H^+$ and electrons to generate carbon monoxide (CO) and $H_2O$.

$$2H_2O \rightarrow 4H^+ + O_2 + 4e^- \quad (1)$$

$$2CO_2 + 4H^+ 4e^- \rightarrow 2CO + 2H_2O \quad (2)$$

On the other hand, an example of a case of a basic solution in which the hydrogen ion concentration of the electrolytic solution is larger than 7 is shown in FIG. 7. In the vicinity of the oxidation catalyst layer 19, a reaction of the following formula (3) occurs. That is, $OH^-$ is oxidized to generate $O_2$, $H_2O$, and electrons. In the vicinity of the reduction catalyst layer 20, a reaction of the following formula (4) occurs. That is, $CO_2$ undergoes a reduction reaction to receive electrons together with $H_2O$, and carbon monoxide (CO) and $OH^-$ are generated. OH⁻ generated on the reduction catalyst layer 20 side moves to the oxidation catalyst layer 19 side via an ion transfer path described below.

  (3)

  (4)

The multijunction solar cell 17 needs to have an open circuit voltage equal to or higher than a potential difference between a standard redox potential of the oxidation reaction occurring in the oxidation catalyst layer 19 and a standard redox potential of the reduction reaction occurring in the reduction catalyst layer 20. For example, when the hydrogen ion concentration (pH) of the reaction solution=0, the standard redox potential of the oxidation reaction in the formula (1) is +1.23 [V], and the standard redox potential of the reduction reaction in the formula (2) Is −0.1 [V]. Therefore, the open circuit voltage of the multijunction solar cell 17 needs to be 1.33 [V] or more.

More preferably, the open circuit voltage needs to be equal to or higher than the potential difference including the overvoltage. More specifically, for example, when each overvoltage of the oxidation reaction in the formula (1) and the reduction reaction in the formula (2) is 0.2 [V], the open circuit voltage is preferably 1.73 [V] or more.

The reduction reaction in the formulae (2) and (4) described above showed the reduction reaction from $CO_2$ to CO, but the present invention is not limited thereto. The reduction reaction from $CO_2$ to HCOOH, HCHO, $CH_4$, $CH_3OH$, $C_2H_5OH$, $HOCH_2CH_2OH$, and the like may also occur. Any reduction reaction consumes H⁺ or generates OH⁻. Therefore, when H⁺ generated in the oxidation catalyst layer 19 cannot move to the reduction catalyst layer 20 of the counter electrode, or when OH⁻ generated in the reduction catalyst layer 20 cannot move to the oxidation catalyst layer 19 of the counter electrode, the overall reaction efficiency is reduced. In contrast, in the chemical reactor according to the present embodiment, movement of H⁺ or OH⁻ can be improved by providing an ion transfer path for transferring H⁺ or OH⁻. Therefore, high photoreaction efficiency can be realized.

Next, a chemical reactor using the photochemical reaction cell described above will be described with reference to FIGS. 8 to 11. Here, the redox reaction (the formula (1) and the formula (2)) in the case of an acidic solution in which the hydrogen ion concentration of the electrolytic solution is smaller than 7 will be described as an example. In the case of a basic solution in which the hydrogen ion concentration of the electrolytic solution is larger than 7, the redox reactions according to the formulae (3) and (4) described above occur.

Figure 8:
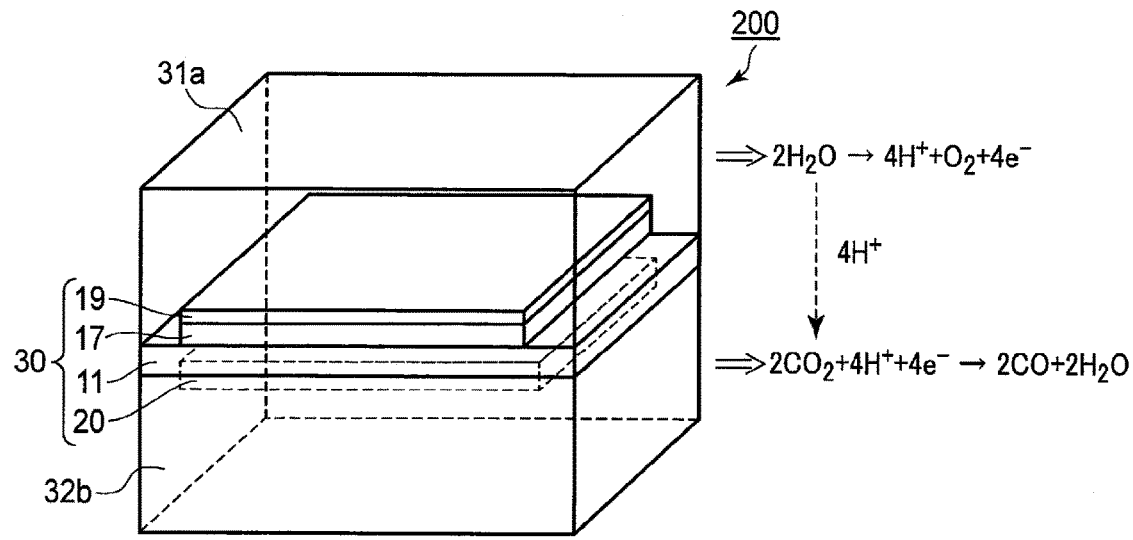
FIG. 8 is a perspective view showing a structure of a chemical reactor according to a third embodiment.
Figure 9:
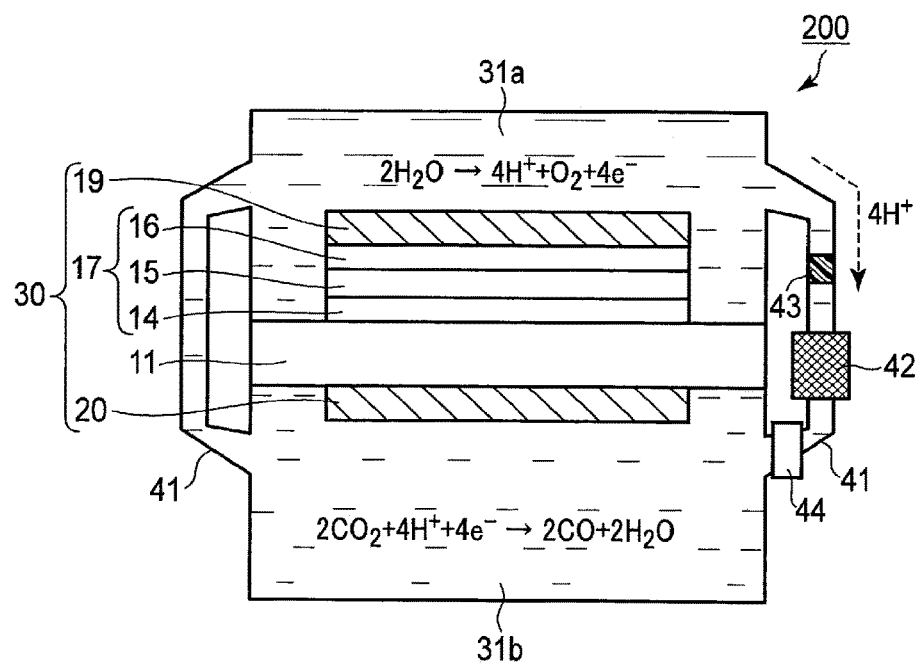
FIG. 9 is a cross-sectional view showing the structure of the chemical reactor according to the third embodiment.

FIG. 8 is a perspective view showing a structure of a chemical reactor 200 according to the present embodiment. FIG. 9 is a cross-sectional view showing the structure of the chemical reactor 200. The chemical reactor 200 includes a photochemical reaction cell 30, an electrolytic bath 31 accommodating the photochemical reaction cell, and an electrolytic bath flow path 41 connected to the electrolytic bath 31 as an ion transfer path. In FIG. 8, the ion transfer path is omitted. As described above, the photochemical reaction cell 30 includes the laminate of the oxidation catalyst layer 19, the reduction catalyst layer 20, the multijunction solar cell 17 formed therebetween, and the substrate 11.

The electrolytic bath 31 includes an oxidation reaction electrolytic bath 31*a* in which the oxidation catalyst layer 19 is disposed and a reduction reaction electrolytic bath 31*b* in which the reduction catalyst layer 20 is disposed. In the oxidation reaction electrolytic bath 31*a*, $H_2O$ is oxidized by the oxidation catalyst layer 19 to generate $O_2$ and H⁺. In the reduction reaction electrolytic bath 31*b*, $CO_2$ is reduced by the reduction catalyst layer 20 to generate CO and $H_2O$. These two electrolytic baths are separated into two by the substrate 11 of the photochemical reaction cell 30. In this example, an end portion of the substrate 11 protrudes from end portions of the multijunction solar cell 17, the oxidation catalyst layer 19, and the reduction catalyst layer 20, but the present invention is not limited thereto. The substrate 11, the multijunction solar cell 17, the oxidation catalyst layer 19, and the reduction catalyst layer 20 may be in the form of a flat plate having the same area.

It is possible to supply different electrolytic solutions to the oxidation reaction electrolytic bath 31*a* and the reduction reaction electrolytic bath 31*b*. The electrolytic bath flow path 41 which enables ion movement connects the oxidation reaction electrolytic bath 31*a* and the reduction reaction electrolytic bath 31*b*.

As described above, according to the structure including the electrolytic bath flow path 41, H⁺ generated on the oxidation catalyst layer 19 side can be transferred to the reduction catalyst layer 20. Due to H⁺, dioxide carbon can be decomposed on the reduction catalyst layer 20 side. Therefore, high photoreaction efficiency can be achieved.

The electrolytic bath flow path 41 will be described in more detail. The electrolytic bath flow paths 41 are provided, for example, on the sides of the electrolytic bath 31. One end of the electrolytic bath flow paths 41 is connected to the oxidation reaction electrolytic bath 31*a* and the other end thereof is connected to the reduction reaction electrolytic bath 31*b*. That is, the electrolytic bath flow path 41 connects the oxidation reaction electrolytic bath 31*a* and the reduction reaction electrolytic bath 31*b*. Due to this, ions can move between the oxidation catalyst layer 19 and the reduction catalyst layer 20.

A part of the electrolytic bath flow path 41 is filled with an ion exchange membrane 43, and the ion exchange membrane 43 passes only specific ions. Therefore, it is possible to move only specific ions while separating the electrolytic solution between the oxidation reaction electrolytic bath 31*a* and the reduction reaction electrolytic bath 31*b*.

The ion exchange membrane 43 is a proton exchange membrane, and can move H⁺ generated in the oxidation reaction electrolytic bath 31*a* to the reduction reaction electrolytic bath 31*b* side. Examples of the proton exchange membrane include a cation exchange membrane such as Nafion or Flemion, and an anion exchange membrane such as Neosceptor or Seremion.

Instead of the ion exchange membrane 43, a material such as agar capable of moving ions and separating the electrolytic solution may be used. For example, a salt bridge is used. In general, when a proton exchangeable solid polymer membrane represented by Nafion is used, ion transfer performance can be improved.

In addition, a circulation mechanism 42 such as a pump may be provided in the electrolytic bath flow path 41. By promoting circulation of the electrolytic solution by the circulation mechanism 42, circulation of ions (H⁺) can be improved between the oxidation reaction electrolytic bath 31*a* and the reduction reaction electrolytic bath 31*b*. In addition, two electrolytic bath flow paths 41 may be provided. By using the circulation mechanism 42 provided in at least one of the electrolytic bath flow paths 41, ions may be moved from the oxidation reaction electrolytic bath 31*a* to the reduction reaction electrolytic bath 31*b* via one electrolytic bath flow path 41, and may be moved from the reduction reaction electrolytic bath 31b to the oxidation reaction electrolytic bath 31a via the other electrolytic bath flow path 41. In addition, a plurality of circulation mechanisms 42 may be provided. In addition, a plurality (three or more) of electrolytic bath flow paths 41 may be provided so as to reduce diffusion of ions and circulate ions more efficiently.

By making the flow of the liquid by the circulation mechanism 42, it is possible to suppress bubbles of the generated gas from staying on the surface of the electrode or the surface of the electrolytic bath and to suppress efficiency reduction and light quantity distribution caused by scattering of sunlight due to bubbles.

In addition, when irradiated with light, heat can be generated on the surface of the multijunction solar cell 17. Convection is generated by using a temperature difference occurring in the electrolytic solution due to heat, and the ions may be circulated more efficiently. In this case, movement of ions can be promoted more than ion diffusion.

A temperature adjustment mechanism 44 for adjusting the temperature of the electrolytic solution may be provided in the electrolytic bath flow path 41 or the electrolytic bath 31. By controlling the temperature using the temperature adjustment mechanism 44, solar cell performance and catalyst performance can be controlled. For example, by making the temperature of the reaction system uniform, the performance of the solar cell or the catalyst can be stabilized and improved. In addition, due to the stability of the system, a temperature rise can be prevented. Due to the temperature control, the selectivity of the solar cell and the catalyst can be changed and the product thereof can be controlled.

The oxidation reaction electrolytic bath 31a is filled with an electrolytic solution including an arbitrary electrolyte. The oxidation catalyst layer 19 is immersed in the electrolytic solution. It is preferable that the electrolytic solution promotes the oxidation reaction of $H_2O$. For example, a liquid including $H_2O$ is used.

The reduction reaction electrolytic bath 31b is filled with an arbitrary electrolytic solution. The reduction catalyst layer 20 is immersed in the electrolytic solution. It is preferable that the electrolytic solution includes a $CO_2$ absorbent which lowers the reduction potential of $CO_2$, has high ion conductivity, and absorbs $CO_2$. For example, a liquid including $CO_2$ is used.

Examples of the electrolytic solution filling the reduction reaction electrolytic bath 31b may include an ionic liquid, which includes a salt of a cation such as an imidazolium ion or a pyridinium ion and an anion such as $BF_4^-$ or $PF_6^-$ and is in a liquid state in a wide temperature range, or an aqueous solution thereof. In addition, examples of the electrolytic solution include an amine solution such as ethanolamine, imidazole, or pyridine, or an aqueous solution thereof. The amine may be any of a primary amine, a secondary amine, and a tertiary amine. Examples of the primary amine include methylamine, ethylamine, propylamine, butylamine, pentylamine, hexylamine, and the like. In any of the primary amine, the secondary amine, and the tertiary amine, a hydrocarbon group substituting the amine may be an alcohol group, or may be substituted with halogen. Examples of these include methanolamine, ethanolamine, and chloromethylamine. The hydrocarbon group substituting the amine may have an unsaturated bond.

Examples of the secondary amine include dimethylamine, diethylamine, dipropylamine, dibutylamine, dipentylamine, dihexylamine, dimethanolamine, diethanolamine, dipropanolamine, methylethylamine, methylpropylamine, and the like.

Examples of the tertiary amines include trimethylamine, triethylamine, tripropylamine, tributylamine, trihexylamine, trimethanolamine, triethanolamine, tripropanolamine, tributanolamine, tripropanolamine, triethanolamine, methyldiethylamine, methyldipropylamine, and the like.

Ions such as imidazolium ions and pyridinium ions can be used as cations of the ionic liquid. Examples of the imidazolium ions include 1-ethyl-3-methylimidazolium ion, 1-methyl-3-propylimidazolium ion, 1-butyl-3-methylimidazole ion, 1-methyl-3-pentylimidazolium ion, 1-hexyl-3-methylimidazolium ion, and the like. The 2-position of these imidazolium ions may be substituted, and examples thereof include 1-ethyl-2,3-dimethylimidazolium ion, 1,2-dimethyl-3-propylimidazolium ion, 1-butyl 2,3-dimethylimidazolium ion, 1,2-dimethyl-3-pentylimidazolium ion, 1-hexyl-2,3-dimethylimidazolium ion, and the like. Examples of the pyridinium ions include methylpyridinium, ethylpyridinium, propylpyridinium, butylpyridinium, pentylpyridinium, hexylpyridinium, and the like. Both the imidazolium ion and the pyridinium ion may be substituted with an alkyl group, and an unsaturated bond may be present.

Examples of the anion of the ionic liquid include a fluoride ion, a chloride ion, a bromide ion, an iodide ion, $BF_4^-$, $PF_6^-$, $CF_3COO^-$, $CF_3SO_3^-$, $NO_3^-$, $SCN^-$, $(CF_3SO_2)_3C^-$, bis(methoxysulfonyl)imide, bis(trifluoromethoxysulfonyl)imide, bis(perfluoroethylsulfonyl)imide, and the like. In addition, it is also possible to use zwitter ions obtained by connecting the cation and the anion of the ionic liquid to hydrocarbon.

The temperature of the electrolytic solution filling the oxidation reaction electrolytic bath 31a and the temperature of the electrolytic solution filling the reduction reaction electrolytic bath 31b may be equal to or different from each other according to the use environment. For example, as the electrolytic solution used for the reduction reaction electrolytic bath 31b, an amine absorbing solution including $CO_2$ discharged from a factory can be used. In this case, the temperature of the electrolytic solution is higher than the ambient temperature, for example, 30° C. to 150° C., more specifically, 40° C. to 120° C.

As the reduction catalyst layer 20, the reduction catalyst 1 in the first embodiment is used. Reduction potential is applied to the metal layer 102 of the reduction catalyst. Therefore, among the electrolytic solution components, particularly $CO_2$-containing ions (for example, bicarbonate ions) or physically dissolved $CO_2$ receive electrostatic attraction in the vicinity of the metal layer 102 and the quaternary nitrogen included in the modified organic molecule 112 fixed on the surface of the metal layer 102. As a result, an electric double layer composed of $CO_2$, and the metal layer 102 and the quaternary nitrogen cation is formed at an interface of the catalyst and the electrolytic solution.

At the interface, a $CO_2$ reduction reaction by a charge transfer reaction proceeds. In the reduction reaction electrolytic bath 31b, $CO_2$ is reduced by the reduction catalyst layer 20 to generate a carbon compound. Specifically, $CO_2$ is converted into carbon monoxide (CO), a formic acid (HCOOH), formaldehyde (HCHO), methanol ($CH_3OH$), an acetic acid ($CH_3COOH$), acetaldehyde ($CH_3CHO$), ethanol ($CH_3CH_2OH$), and ethylene glycol ($HOCH_2CH_2OH$). In addition, moisture ($H_2O$) is reduced as a side reaction, and hydrogen ($H_2$) can also be generated.

When carbon dioxide undergoes a two-electron reduction reaction, a formic acid as well as carbon monoxide is generated. When the formic acid undergoes a two-electron reduction reaction, formaldehyde is formed. Furthermore, when the formaldehyde undergoes a two-electron reduction reaction, methanol is generated. When methanol is generated by using the reduction catalyst 1, a formic acid or formaldehyde, as well as carbon dioxide, may be selected as the reducing raw material. Therefore, it is desirable that at least one reducing raw material selected from the carbon dioxide, the formic acid, and the formaldehyde is absorbed in the electrolytic solution in the reduction reaction electrolytic bath 31b. Examples of the electrolytic solution in the reduction reaction electrolytic bath 31b include a sodium hydrogencarbonate solution.

In addition, when carbon dioxide undergoes a two-electron reduction reaction, an oxalic acid may be generated. When the oxalic acid undergoes a two-electron reduction reaction, a glycolic acid is generated. Furthermore, when the glycolic acid undergoes a two-electron reduction reaction, a glyoxal or glycolic acid is generated. Further, when the glyoxal or glycolic acid undergoes two-electron reduction reaction, glycolaldehyde is generated. Further, when the glycolaldehyde undergoes a two-electron reduction reaction, ethylene glycol is generated. When the ethylene glycol is generated by using the reduction catalyst 1, an oxalic acid, a glycolic acid, or a glycol aldehyde, as well as carbon dioxide, may be selected as a reducing raw material. Therefore, at least one reducing raw material selected from the oxalic acid, the glycolic acid, and the glycol aldehyde may be absorbed in the electrolytic solution in the reduction reaction electrolytic bath 31b.

When carbon dioxide undergoes an eight-electron reduction reaction, an acetic acid may be generated. When the acetic acid undergoes an eight-electron reduction reaction, acetaldehyde is formed. Further, when the acetaldehyde undergoes an eight-electron reduction reaction, ethanol is generated. When the ethanol is generated by using the reduction catalyst 1, an acetic acid or acetaldehyde, as well as carbon dioxide, may be selected as a reducing raw material. Therefore, at least one reducing material selected from carbon dioxide, acetic acid, and acetaldehyde may be absorbed in the electrolytic solution in the reduction reaction electrolytic bath 31b.

As described above, the reaction in which the carbon dioxide is reduced to generate the formic acid, the formaldehyde, and the methanol, the reaction in which the carbon dioxide is reduced to generate the oxalic acid, the glycolic acid, the glyoxal or the glycolic acid, the glycolaldehyde, and the ethylene glycol, and the reaction in which the carbon dioxide is reduced to generate the acetic acid, the acetaldehyde, and the ethanol depend on the density of the modified organic molecules 112 in the reduction catalyst 1. For example, when the density of the modified organic molecules 112 with respect to the metal layer 102 is $1\times10^{11}$ atoms/cm$^2$ or less, a reaction to mainly generate a formic acid, formaldehyde, and methanol occurs. On the other hand, for example, when the density of the modified organic molecules 112 is $1\times10^{12}$ atoms/cm$^2$ to $1\times10^{15}$ atoms/cm$^2$, a reaction to generate an acetic acid, acetaldehyde, and ethanol as well as a formic acid, formaldehyde, and methanol occurs. In particular, when the density of the modified organic molecules 112 is $1\times10^{13}$ atoms/cm$^2$ to $1\times10^{15}$ atoms/cm$^2$, a reaction to mainly generate an acetic acid, acetaldehyde, and ethanol occurs. As shown in Examples described below, the relationship between the molecular density of the organic molecules and the product was found as a result of repeated experiments and investigations by the present inventors.

The binding state and molecular density of the modified organic molecules 112 can be calculated based on analysis result by X-ray photoelectron spectroscopy (XPS). The analysis conditions can be as follows. Note that an detection angle indicates an angle formed between a sample normal and a detector input lens axis.

| Used Model | Quantera-SXM manufactured by PHI |
|---|---|
| Radiated X-ray source | Single crystal spectroscopy AlKα ray |
| Output | 50 W |
| Analysis area | φ200 μm |
| Pass Energy | Wide Scan - 280.0 eV (1.0 eV/Step) |
| | Narrow Scan - 69.0 eV (0.125 eV/Step) |
| Detection angle | 45° |

Charge neutralization electron gun Ar$^+$, e$^-$ used together

As a charge correction (horizontal axis energy correction), a C—C/H bond component of C1s spectrum is adjusted to 284.80 eV.

The bond density (molecular density) of the modified organic molecules 112 is calculated by the following formula (6) from the number of Au atoms per unit area approximated from the following formula (5) and the number of S atoms (S/Au) normalized by the number of Au atoms in a semi-quantitative analysis result.

$$\text{Au(atoms/cm}^2) = \text{density(g/cm}^3) \times \text{detection depth (nm)} \times N/Mw \quad (5)$$

$$\text{Molecular density(atoms/cm}^2) = \text{Au(atoms/cm}^2) \times \text{S/Au (atomic ratio)} \quad (6)$$

Here, the density is 19.3 g/cm$^3$, the detection depth is 5 nm, N is Avogadro's number (atoms/mol), and Mw is 197 g/mol.

In the reduction catalyst 1, the reaction in which carbon dioxide is reduced to generate ethylene glycol via an oxalic acid, a glycolic acid, or glycolaldehyde selectively occurs as the electrode is held at reduction potential. That is, by holding the electrode at the reduction potential, the orientation of the modified organic molecules 112 becomes uniform, and thus, the reaction for generating ethylene glycol occurs. As the electrolysis conditions for holding the electrode at the reduction potential, in a three-electrode cell using an electrode substrate as a working electrode, silver/silver chloride as a reference electrode, and Pt as a counter electrode, it is preferable that a potential of −0.8 V to −1.3 V is applied to the working electrode for 5 hours or more, more preferably 3 hours or more, and still more preferably 1 hour or more. The orientation of the modified organic molecules 112 can be observed by using a scanning tunneling microscope (STM).

Next, a modification example of the chemical reactor according to the present embodiment will be described. FIG. 10 is a cross-sectional view showing the structure of the chemical reactor 210. FIG. 11 is a cross-sectional view showing the structure of the chemical reactor 220. In the following, a structure different from that of the above-described chemical reactor 200 will be described.

As shown in FIG. 10, the chemical reactor 210 includes a photochemical reaction cell 30, an electrolytic bath 31 accommodating the photochemical reaction cell 30, and an opening 51 formed in a substrate 11 as an ion transfer path.

The opening 51 is provided so as to penetrate an end portion of the substrate 11 from an oxidation reaction electrolytic bath 31a side to a reduction reaction electrolytic bath 31b side. An ion exchange membrane 43 is filled in a part of the opening 51, and the oxidation reaction electrolytic bath 31a and the reduction reaction electrolytic bath 31b are separated from each other by the substrate 11 and the ion exchange membrane 43. The ion exchange membrane 43 passes only specific ions.

With such a configuration, it is possible to move only specific ions via the ion exchange membrane 43 while separating an electrolytic solution between the oxidation reaction electrolytic bath 31a and the reduction reaction electrolytic bath 31b.

As shown in FIG. 11, the chemical reactor 220 includes a photochemical reaction cell 30, an electrolytic bath 31 accommodating the photochemical reaction cell 30, and an opening 52 formed as an ion transfer path. The opening 52 is provided so as to penetrate a reduction catalyst layer 20, a substrate 11, a multifunction solar cell 17, and an oxidation catalyst layer 19 from an oxidation reaction electrolytic bath 31a side to a reduction reaction electrolytic bath 31b side.

An ion exchange membrane 43 is filled in a part of the opening 52, and the oxidation reaction electrolytic bath 31a and the reduction reaction electrolytic bath 31b are separated from each other by the substrate 11 and the ion exchange membrane 43. The ion exchange membrane 43 passes only specific ions.

With such a configuration, it is possible to move only specific ions via the ion exchange membrane 43 while separating an electrolytic solution between the oxidation reaction electrolytic bath 31a and the reduction reaction electrolytic bath 31b.

In the chemical reactor 220 of FIG. 11, the ion exchange membrane 43 is provided only in a part of the opening 52, but the ion exchange membrane 43 may be provided in the entire opening 52.

As described above, according to the present embodiment, a chemical reactor with high reaction efficiency can be provided.

EXAMPLES

Example 1

A reduction catalyst of Example 1 was prepared by making a substrate surface (metal layer) of Au and using 1-(2-mercaptoethyl)-4-(3-aminopropyl)-pyridinium bromide as a modified organic molecule.

First, a stainless steel substrate (150 mm×250 mm, thickness: 150 µm) was used as a current collector, and a metal layer including Au was formed on a surface thereof by sputtering. The metal layer had a uniform thickness in a planar direction, and a film thickness thereof was 100 nm.

Next, the current collector, on which the metal layer was formed, was immersed in an ethanol solution including 10 mL of 1-(2-mercaptoethyl)-4-(3-aminopropyl)-pyridinium bromide at a concentration of 1 mM for 48 hours, so as to fix the modified organic molecule on the surface of the metal layer.

The fact that the modified organic molecule was fixed to the metal layer was confirmed by measuring electrochemical responses of the current collector before and after the process of fixing the modified organic molecule. More details are as follows.

First, a three-electrode cell was constructed by using a current collector including a metal layer including Au as a working electrode, an Ag/AgCl electrode as a reference electrode, and a Pt electrode as a counter electrode. A 0.2 M potassium chloride (KCl) aqueous solution in which 1 mM of hexaammine ruthenium (III) chloride ($[Ru(NH_3)_6]Cl_3$) was dissolved was used as an electrolytic solution. By using the three-electrode cell, the response of the redox current of hexaammine ruthenium (III) anion was measured. As the measurement conditions, a potential range was −0.5 V to +0.1 V with respect to Ag/AgCl, and a scanning speed was 100 mV/sec.

In the three-electrode cell using the current collector before the modified organic molecule was fixed, a reversible redox current of a redox species was observed. On the other hand, the redox reaction was not observed in the three-electrode cell using the current collector to which the modified organic molecule was fixed. It is considered that the disappearance of the electrochemical redox reaction of the hexaammine ruthenium (III) cation is caused by the shielding effect based on the formation of the modified organic molecule.

Examples 2 to 10

Reduction catalysts of Examples 2 to 10 were prepared in the same manner as in Example 1, except that metal layers were made of materials shown in Table 1.

Comparative Examples 1 to 10

Reduction catalysts of Comparative Examples 1 to 10 were prepared in the same manner as in Example 1, except that metal layers were made of materials shown in Table 1 and modified organic molecules were not used.

Comparative Example 11

A reducing catalyst of Comparative Example 11 was prepared in the same manner as in Example 1, except that a metal layer was made of Au and 1-(2-mercaptoethyl)-4-butylpyridinium bromide was used as a modified organic molecule.

Comparative Examples 12 to 20

Reduction catalysts of Comparative Examples 12 to 20 were prepared in the same manner as in Comparative Example 11, except that metal layers were made of materials shown in Table 1.

<Production of Three-electrode Cell>

Three-electrode cells were produced by using reduction catalysts in Examples 1 to 10 and Comparative Examples 1 to 20.

The three-electrode cell using an H type cell was constructed by using the reduction catalyst of each Example and each Comparative Example as a working electrode, an Ag/AgCl electrode as a reference electrode, and a Pt electrode as a counter electrode. The Pt electrode was disposed in a cell partitioned by a glass filter.

100% $CO_2$ gas was bubbled in a 5% $NaHCO_3$ aqueous solution, and $CO_2$ was dissolved until a $CO_2$ concentration absorbed by the solution reached saturation. Concentrations of the $CO_2$ gas absorbed in the 5% $NaHCO_3$ aqueous solution at an inlet and an outlet were measured, and when the concentrations reached the same concentration, it was determined that the concentration in the aqueous solution reached the saturated concentration. The 5% $NaHCO_3$ aqueous solution prepared as described above was used as a $CO_2$ absorbent for the three-electrode cell and the electrolytic solution for $CO_2$ reduction.

[Evaluation of CO$_2$ Reduction Performance]

For each of the three-electrode cells of Examples 1 to 10 and Comparative Examples 1 to 20 prepared as described above, the CO$_2$ reduction performance was evaluated as follows.

Constant current electrolysis was performed on the three-electrode cell so that the potential applied to the working electrode was −1.2 V with respect to Ag/AgCl, and current values flowing through the working electrode and the counter electrode were measured. The electrolysis time was 60 minutes. During the measurement, 100% CO$_2$ gas was bubbled into an electrolysis chamber of the working electrode, and the mixture was stirred at a stirring speed of 800 rpm by using a magnetic stirrer. The measurement was performed by using an electrochemical measurement apparatus (Solartron Cell Test System, manufactured by Toyo Technica Co., Ltd.).

Next, reduction products generated by the constant current electrolysis were analyzed. As gas components, a hydrogen gas and a carbon monoxide gas were analyzed. Gas components were analyzed by gas chromatography (Varian Micro GC CP 4900). A formic acid, formaldehyde, methanol, an acetic acid, acetaldehyde, ethanol, an oxalic acid, a glycolic acid, glycolaldehyde, and ethylene glycol were analyzed as the reduction products dissolved in the electrolytic solution.

The formic acid, the acetic acid, the oxalic acid, and the glycolic acid were analyzed by ion chromatography (DX-320, manufactured by Thermo Fisher Scientific). Formaldehyde, acetaldehyde, and glycolaldehyde were analyzed by high performance liquid chromatography (ACQUITY UPLC, manufactured by Waters). Methanol and ethanol were analyzed by gas chromatography mass spectrometry (6890/5975, manufactured by Agilent). Ethylene glycol was analyzed by gas chromatography (6890, manufactured by Agilent).

Faraday efficiency was calculated based on the quantitative analysis of the current consumed in the reduction reaction at the working electrode and the generated reduction product. The Faraday efficiency is expressed by a ratio of the quantity of electricity required for the production of the reduction product to the quantity of electricity supplied. The Faraday efficiency of each of the analyzed reduction products was taken as selectivity (%) of each reduction product. In addition, the total Faraday efficiency of all reduction products was calculated and taken as a CO$_2$ reduction ratio. The CO$_2$ reduction rate does not become 100%. This is because a part of the amount of electrons injected is consumed for hydrogen production and Joule heat due to side reactions.

Table 1 shows the results of CO$_2$ reduction performance for Examples 1 to 10 and Comparative Examples 1 to 20.

TABLE 1

| | Metal layer | Modified organic molecule | CO | HCOOH HCHO CH$_3$OH | CH$_3$COOH CH$_3$CHO CH$_3$CH$_2$OH | Oxalic acid Glycolic acid Glycol aldehyde Ethylene glycol | CO$_2$ reduction ratio |
|---|---|---|---|---|---|---|---|
| Ex. 1 | Au | 1-(2-mercaptoethyl)-<br>4-(3-aminopropyl)-<br>pyridinium bromide | 3 | 1<br>1<br>1 | 1<br>1<br>2 | 1<br>1<br>1<br>62 | 75 |
| Ex. 2 | Ag | 1-(2-mercaptoethyl)-<br>4-(3-aminopropyl)-<br>pyridinium bromide | 3 | 1<br>1<br>1 | 1<br>1<br>2 | 1<br>1<br>1<br>60 | 73 |
| Ex. 3 | Cu | 1-(2-mercaptoethyl)-<br>4-(3-aminopropyl)-<br>pyridinium bromide | 3 | 1<br>1<br>1 | 1<br>1<br>2 | 1<br>1<br>1<br>57 | 70 |
| Ex. 4 | Zn | 1-(2-mercaptoethyl)-<br>4-(3-aminopropyl)-<br>pyridinium bromide | 3 | 1<br>1<br>1 | 1<br>1<br>2 | 1<br>1<br>1<br>60 | 73 |
| Ex. 5 | Pt | 1-(2-mercaptoethyl)-<br>4-(3-aminopropyl)-<br>pyridinium bromide | 3 | 1<br>1<br>1 | 1<br>1<br>2 | 1<br>1<br>1<br>57 | 70 |
| Ex. 6 | Fe | 1-(2-mercaptoethyl)-<br>4-(3-aminopropyl)-<br>pyridinium bromide | 3 | 1<br>1<br>1 | 1<br>1<br>2 | 1<br>1<br>1<br>61 | 74 |
| Ex. 7 | Ti | 1-(2-mercaptoethyl)-<br>4-(3-aminopropyl)-<br>pyridinium bromide | 3 | 1<br>1<br>1 | 1<br>1<br>2 | 1<br>1<br>1<br>57 | 70 |
| Ex. 8 | Ni | 1-(2-mercaptoethyl)-<br>4-(3-aminopropyl)-<br>pyridinium bromide | 3 | 1<br>1<br>1 | 1<br>1<br>2 | 1<br>1<br>1<br>64 | 77 |
| Ex. 9 | Sn | 1-(2-mercaptoethyl)-<br>4-(3-aminopropyl)-<br>pyridinium bromide | 3 | 1<br>1<br>1 | 1<br>1<br>2 | 1<br>1<br>1<br>53 | 66 |

TABLE 1-continued

| | | Modified organic molecule | CO | Selectivity (%) HCOOH HCHO CH$_3$OH | CH$_3$COOH CH$_3$CHO CH$_3$CH$_2$OH | Oxalic acid Glycolic acid Glycol aldehyde Ethylene glycol | CO$_2$ reduction ratio |
|---|---|---|---|---|---|---|---|
| Ex. 10 | In | 1-(2-mercaptoethyl)-4-(3-aminopropyl)-pyridinium bromide | 3 | 1<br>1<br>1 | 1<br>1<br>2 | 1<br>1<br>1<br>52 | 65 |
| | Substrate surface | | | | | | |
| Comp. Ex. 1 | Au | — | 30 | — | — | — | 30 |
| Comp. Ex. 2 | Ag | — | 30 | — | — | — | 30 |
| Comp. Ex. 3 | Cu | — | 25 | — | — | — | 25 |
| Comp. Ex. 4 | Zn | — | 10 | — | — | — | 10 |
| Comp. Ex. 5 | Pt | — | — | — | — | — | — |
| Comp. Ex. 6 | Fe | — | — | — | — | — | — |
| Comp. Ex. 7 | Ti | — | — | — | — | — | — |
| Comp. Ex. 8 | Ni | — | — | — | — | — | — |
| Comp. Ex. 9 | Sn | — | — | — | — | — | — |
| Comp. Ex. 10 | In | — | — | — | — | — | — |
| Comp. Ex. 11 | Au | 1-(2-mercaptoethyl)-4-butylpyridinium bromide | 2 | 1<br>1<br>2 | 41<br>7<br>3 | 1<br>1<br>1<br>5 | 65 |
| Comp. Ex. 12 | Ag | 1-(2-mercaptoethyl)-4-butylpyridinium bromide | 2 | 1<br>1<br>2 | 39<br>7<br>3 | 1<br>1<br>1<br>5 | 63 |
| Comp. Ex. 13 | Cu | 1-(2-mercaptoethyl)-4-butylpyridinium bromide | 2 | 1<br>1<br>2 | 36<br>7<br>3 | 1<br>1<br>1<br>5 | 60 |
| Comp. Ex. 14 | Zn | 1-(2-mercaptoethyl)-4-butylpyridinium bromide | 2 | 1<br>1<br>2 | 39<br>7<br>3 | 1<br>1<br>1<br>5 | 63 |
| Comp. Ex. 15 | Pt | 1-(2-mercaptoethyl)-4-butylpyridinium bromide | 2 | 1<br>1<br>2 | 36<br>7<br>3 | 1<br>1<br>1<br>5 | 60 |
| Comp. Ex. 16 | Fe | 1-(2-mercaptoethyl)-4-butylpyridinium bromide | 2 | 1<br>1<br>2 | 40<br>7<br>3 | 1<br>1<br>1<br>5 | 64 |
| Comp. Ex. 17 | Ti | 1-(2-mercaptoethyl)-4-butylpyridinium bromide | 2 | 1<br>1<br>2 | 36<br>7<br>3 | 1<br>1<br>1<br>5 | 60 |
| Comp. Ex. 18 | Ni | 1-(2-mercaptoethyl)-4-butylpyridinium bromide | 2 | 1<br>1<br>2 | 43<br>7<br>3 | 1<br>1<br>1<br>5 | 67 |
| Comp. Ex. 19 | Sn | 1-(2-mercaptoethyl)-4-butylpyridinium bromide | 2 | 1<br>1<br>2 | 32<br>7<br>3 | 1<br>1<br>1<br>5 | 56 |
| Comp. Ex. 20 | In | 1-(2-mercaptoethyl)-4-butylpyridinium bromide | 2 | 1<br>1<br>2 | 31<br>7<br>3 | 1<br>1<br>1<br>5 | 55 |

All of Examples 1 to 10 showed extremely high $CO_2$ reduction rates. Further, in Examples 1 to 10, ethylene glycol was generated with very high selectivity. It is considered that the amino group at the terminal of the modified organic molecule promotes the reduction reaction of $CO_2$ and contributes to the improvement of the selectivity of ethylene glycol.

Comparative Examples 1 to 4 are reduction electrodes which have no modified organic molecules. In each of Comparative Examples 1 to 4, the $CO_2$ reduction ratio was extremely low. Comparative Examples 5 to 10 are reduction electrodes which have no modified organic molecule and have a metal layer made of Pt, Fe, Ti, Ni, Sn, or In. In each of Comparative Examples 5 to 10, $CO_2$ was not reduced.

Comparative Examples 11 to 20 are reduction electrodes using modified organic molecules which have no amino group at their terminals. Comparative examples 11 to 20 showed relatively high $CO_2$ reduction rates, but a large amount of an acetic acid, acetaldehyde, and ethanol was generated as the reduction products. In addition, selectivity thereof was not high.

Example 11

The reduction catalyst of Example 11 was produced by making a surface (metal layer) of a base material of Au, using 1-(2-mercaptoethyl)-3-aminomethylimidazolium bromide as spacer organic molecules and modified organic molecules, and using Au particles having an average particle diameter of 3 nm as metal fine particles. The average particle diameter of the metal fine particles was measured by using a particle size distribution meter (Zetasizer Nano ZS, manufactured by Malvern).

First, a stainless steel substrate (150 mm×250 mm, thickness: 150 μm) was used as a current collector, and a metal layer made of Au was formed on a surface thereof by sputtering. The metal layer had a uniform thickness in a planar direction, and a film thickness thereof was 100 nm.

Next, the current collector, on which the metal layer was formed, was immersed in an ethanol solution including 10 mL of 1-(2-mercaptoethyl)-3-aminomethylimidazolium bromide at a concentration of 1 mM for 48 hours, so that spacer organic molecules were fixed on the surface of the metal layer to form a spacer organic molecular layer.

The fact that the spacer organic molecule was fixed to the metal layer was confirmed by measuring electrochemical responses of the current collector before and after the process of fixing the spacer organic molecule. More details are as follows.

First, a three-electrode cell was constructed by using a current collector including a metal layer made of Au as a working electrode, an Ag/AgCl electrode as a reference electrode, and a Pt electrode as a counter electrode. A 0.2 M potassium chloride (KCl) aqueous solution in which 1 mM of hexaammine ruthenium (III) chloride ($[Ru(NH_3)_6]Cl_3$) was dissolved was used as an electrolytic solution. By using the three-electrode cell, the response of the oxidation-reduction current of hexaammine ruthenium(III) anion was measured. As the measurement conditions, a potential range was −0.5 V to +0.1 V with respect to Ag/AgCl, and a scanning speed was 100 mV/sec.

In the three-electrode cell using the current collector before the spacer organic molecule was fixed, a reversible oxidation-reduction current of a redox species was observed. On the other hand, the redox reaction was not observed in the three-electrode cell using the current collector to which the spacer organic molecule was fixed. It is considered that the disappearance of the electrochemical redox reaction of the hexaammine ruthenium (III) cation is caused by the shielding effect of the spacer organic molecule.

Next, the current collector, on which the spacer organic molecular layer was formed, was immersed in an aqueous solution in which metal fine particles were dispersed for 12 hours to fix the metal fine particles on the surface of the spacer organic molecular layer. The fact that the metal fine particles were fixed was confirmed by measuring electrochemical responses of the current collector before and after the process of fixing the metal fine particles. More details are as follows.

First, a three-electrode cell was constructed by using a current collector to which the metal fine particles are fixed as a working electrode, an Ag/AgCl electrode as a reference electrode, and a Pt electrode as a counter electrode. A 0.2 M potassium chloride (KCl) aqueous solution in which 1 mM of hexaammine ruthenium (III) chloride ($[Ru(NH_3)_6]Cl_3$) was dissolved was used as an electrolytic solution. By using the three-electrode cell, the response of the oxidation-reduction current of hexaammine ruthenium (III) anion was measured. As the measurement conditions, a potential range was −0.5 V to +0.1 V with respect to Ag/AgCl, and a scanning speed was 100 mV/sec.

In the current collector before the metal fine particles are fixed, a reversible redox current of a redox species was not observed due to the shielding effect by the spacer organic molecular layer. However, in the current collector on which the metal fine particles were fixed, the redox reaction was observed again. It was confirmed that the metal fine particles were fixed on the surface of the spacer organic molecular layer by observing the electrochemical redox reaction of the hexaammine ruthenium (III) cation.

Next, the current collector, on which the metal fine particles were fixed, was immersed in an ethanol solution including 10 mL of 1-(2-mercaptoethyl)-3-aminomethylimidazolium bromide at a concentration of 1 mM for 48 hours, so as to fix the modified organic molecules on the surfaces of the metal fine particles.

The fact that the modified organic molecules were fixed on the surfaces of the metal fine particles was confirmed by the same method as the above-described method for confirming that the spacer organic molecules were fixed. Before the modified organic molecules were fixed on the metal fine particles, a reversible redox current of a redox species was observed, but no redox reaction was observed after the modified organic molecules are fixed. It is considered that the disappearance of the electrochemical redox reaction of the hexaammine ruthenium (III) cation is caused by the shielding effect of the modified organic molecule.

After that, in order to increase the amount of the fixed metal fine particles, the fixing of the metal fine particles and the fixing of the modified organic molecules were repeated ten times.

Example 12

The reduction catalyst of Example 12 was prepared in the same manner as in Example 11, except that 1-(6-mercaptohexyl)-3-aminomethylimidazolium bromide was used as a spacer organic molecule and a modified organic molecule.

Example 13

The reduction catalyst of Example 13 was prepared in the same manner as in Example 11, except that 1-(12-mercaptododecyl)-3-aminomethylimidazolium bromide was used as a spacer organic molecule and a modified organic molecule.

Example 14

The reduction catalyst of Example 14 was prepared in the same manner as in Example 11, except that 1-(2-mercaptoethyl)-3-(2-aminoethyl)imidazolium bromide was used as a spacer organic molecule and a modified organic molecule.

Example 15

The reduction catalyst of Example 15 was prepared in the same manner as in Example 11, except that 1-(2-mercaptoethyl)-3-(4-aminobutyl)imidazolium bromide was used as a spacer organic molecule and a modified organic molecule.

Example 16

The reduction catalyst of Example. 16 was prepared in the same manner as in Example 11, except that 1-(2-mercaptoethyl)-3-(10-aminodecyl)imidazolium bromide was used as a spacer organic molecule and a modified organic molecule.

Example 17

The reduction catalyst of Example 17 was prepared in the same manner as in Example 11, except that 1-(2-mercaptoethyl)-4-(4-aminobutyl)pyridinium bromide was used as a spacer organic molecule and a modified organic molecule.

Example 18

The reduction catalyst of Example 18 was prepared in the same manner as in Example 11, except that 1-(2-mercaptoethyl)-1-(6-aminohexyl)pyrrolidinium bromide was used as a spacer organic molecule and a modified organic molecule.

Example 19

The reduction catalyst of Example 19 was prepared in the same manner as in Example 11, except that 1-(2-mercaptoethyl)-1-(8-aminooctyl)piperidinium bromide was used as a spacer organic molecule and a modified organic molecule.

Example 20

The reduction catalyst of Example 20 was prepared in the same manner as in Example 11, except that 2-mercaptoethyl-(10-aminodecyl)dimethylammonium bromide was used as a spacer organic molecule and a modified organic molecule.

Example 21

The reduction catalyst of Example 21 was prepared in the same manner as in Example 11, except that 1-(4-mercaptobutyl)-3-(2-methylaminoethyl)imidazolium bromide was used as a spacer organic molecule and a modified organic molecule.

Example 22

The reduction catalyst of Example 22 was prepared in the same manner as in Example 11, except that 1-(9-mercaptononyl)-4-(4-dimethylaminobutyl)pyridinium bromide was used as a spacer organic molecule and a modified organic molecule.

Comparative Example 21

The reduction catalyst of Comparative Example 21 was prepared in the same manner as in Example 11, except that 1-(2-mercaptoethyl)-3-ethylimidazolium bromide was used as a spacer organic molecule and a modified organic molecule.

Comparative Example 22

The reduction catalyst of Comparative Example 22 was prepared in the same manner as in Example 11, except that 1-(2-mercaptoethyl)-4-pentylpyridinium bromide was used as a spacer organic molecule and a modified organic molecule.

Comparative Example 23

The reduction catalyst of Comparative Example 23 was prepared in the same manner as in Example 11, except that 1-(2-mercaptoethyl)-1-heptylpyrrolidinium bromide was used as a spacer organic molecule and a modified organic molecule.

Comparative Example 24

The reduction catalyst of Comparative Example 24 was prepared in the same manner as in Example 11, except that 1-(2-mercaptoethyl)-1-nonylpiperidinium bromide was used as a spacer organic molecule and a modified organic molecule.

Comparative Example 25

The reduction catalyst of Example 25 was prepared in the same manner as in Example 11, except that 2-mercaptoethyl-undecyldimethylammonium bromide was used as a spacer organic molecule and a modified organic molecule.

[Evaluation of $CO_2$ Reduction Performance]

$CO_2$ reduction performance was evaluated by using the reduction catalysts in Examples 11 to 22 and Comparative Examples 21 to 25 as the reduction electrode. The evaluation was performed in the same manner as described above. The results thereof are shown in FIG. 2. For reference, the result of Comparative Example 1 is also shown in Table 2.

TABLE 2

| | Spacer organic molecule | Av. particle diameter of metal fine particle (nm) | Modified organic molecule | Selectivity (%) | | | | $CO_2$ reduction ratio |
|---|---|---|---|---|---|---|---|---|
| | | | | CO | HCOOH HCHO $CH_3OH$ | $CH_3COOH$ $CH_3CHO$ $CH_3CH_2OH$ | Oxalic acid Glyoxylic acid Glycol aldehyde Ethylene glycol | |
| Ex. 11 | 1-(2-mercaptoethyl)-3-aminomethylimidazolium bromide | 3 | 1-(2-mercaptoethyl)-3-aminomethylimidazolium bromide | 3 | 1 1 1 | 1 1 2 | 1 1 1 | 85 |

72

TABLE 2-continued

| | Spacer organic molecule | Av. particle diameter of metal fine particle (nm) | Modified organic molecule | Selectivity (%) CO | HCOOH / HCHO / CH$_3$OH | CH$_3$COOH / CH$_3$CHO / CH$_3$CH$_2$OH | Oxalic acid / Glyoxylic acid / Glycol aldehyde / Ethylene glycol | CO$_2$ reduction ratio |
|---|---|---|---|---|---|---|---|---|
| Ex. 12 | 1-(6-mercaptohexyl)-3-aminomethylimidazolium bromide | 3 | 1-(6-mercaptohexyl)-3-aminomethylimidazolium bromide | 3 | 1 / 1 / 1 | 1 / 1 / 2 | 1 / 1 / 1 / 57 | 70 |
| Ex. 13 | 1-(12-mercaptododecyl)-3-aminomethylimidazolium bromide | 3 | 1-(12-mercaptododecyl)-3-aminomethylimidazolium bromide | 3 | 1 / 1 / 1 | 1 / 1 / 2 | 1 / 1 / 1 / 50 | 63 |
| Ex. 14 | 1-(2-mercaptoethyl)-3-(2-aminoethyl)imidazolium bromide | 3 | 1-(2-mercaptoethyl)-3-(2-aminoethyl)imidazolium bromide | 3 | 1 / 1 / 1 | 1 / 1 / 2 | 1 / 1 / 1 / 67 | 80 |
| Ex. 15 | 1-(2-mercaptoethyl)-3-(4 aminobutyl)imidazolium bromide | 3 | 1-(2-mercaptoethyl)-3-(4-aminobutyl)imidazolium bromide | 3 | 1 / 1 / 1 | 1 / 1 / 2 | 1 / 1 / 1 / 61 | 74 |
| Ex. 16 | 1-(2-mercaptoethyl)-3-(10-aminodecyl)imidazolium bromide | 3 | 1-(2-mercaptoethyl)-3-(10-aminodecyl)imidazolium bromide' | 3 | 1 / 1 / 1 | 1 / 1 / 2 | 1 / 1 / 1 / 54 | 67 |
| Ex. 17 | 1-(2-mercaptoethyl)-4-(4-aminobutyl)pyridinium bromide | 3 | 1-(2-mercaptoethyl)-4-(4-aminobutyl)pyridinium bromide | 3 | 1 / 1 / 2 | 1 / 1 / 1 | 1 / 1 / 1 / 59 | 72 |
| Ex. 18 | 1-(2-mercaptoethyl)-1-(6-aminohexyl)pyrrolidinium bromide | 3 | 1-(2-mercaptoethyl)-1-(6-aminohexyl)pyrrolidinium bromide | 3 | 1 / 1 / 1 | 1 / 2 / 1 | 1 / 1 / 1 / 55 | 68 |
| Ex. 19 | 1-(2-mercaptoethyl)-1-(8-aminooctyl)piperidinium bromide | 3 | 1-(2-mercaptoethyl)-1-(8-aminooctyl)piperidinium bromide | 3 | 1 / 2 / 1 | 1 / 1 / 1 | 1 / 1 / 1 / 46 | 59 |
| Ex. 20 | 2-mercaptoethyl-(10-aminodecyl)dimethyl-ammonium bromide' | 3 | 2-mercaptoethyl-(10-aminodecyl)dimethyl-ammonium bromide | 3 | 2 / 1 / 1 | 1 / 1 / 1 | 1 / 1 / 1 / 39 | 52 |
| Ex. 21 | 1-(4-mercaptobutyl)-3-(2-methylaminoethyl)imid-azolium bromide | 3 | 1-(4-mercaptobutyl)-3-(2-methylaminoethyl)imid-azolium bromide | 3 | 1 / 1 / 1 | 1 / 1 / 2 | 1 / 1 / 1 / 50 | 63 |
| Ex. 22 | 1-(9-mercaptononyl)-4-(4-dimethylaminobutyl)py-ridinium bromide | 3 | 1-(9-mercaptononyl)-4-(4-dimethylaminobutyl)py-ridinium bromide | 3 | 1 / 1 / 2 | 1 / 1 / 1 | 1 / 1 / 1 / 40 | 53 |
| Comp. Ex. 1 | — | — | — | 30 | — | — | — | 30 |
| Comp. Ex. 21 | 1-(2-mercaptoethyl)-3-ethylimidazolium bromide | 3 | 1-(2-mercaptoethyl)-3-ethylimidazolium bromide | 2 | 2 / 1 / 1 | 45 / 8 / 3 | 1 / 1 / 1 / 5 | 70 |
| Comp. Ex. 22 | 1-(2-mercaptoethyl)-4-pentylpyridinium bromide | 3 | 1-(2-mercaptoethyl)-4-pentylpyridinium bromide | 2 | 1 / 1 / 2 | 40 / 7 / 3 | 1 / 1 / 1 / 5 | 64 |
| Comp. Ex. 23 | 1-(2-mercaptoethyl)-1-heptylpyrrolidinium bromide | 3 | 1-(2-mercaptoethyl)-1-heptylpyrrolidinium bromide | 2 | 2 / 1 / 1 | 38 / 6 / 2 | 1 / 1 / 1 / 4 | 59 |
| Comp. Ex. 24 | 1-(2-mercaptoethyl)-1-nonylpiperidinium bromide | 3 | 1-(2-mercaptoethyl)-1-nonylpiperidinium bromide | 2 | 1 / 2 / 1 | 37 / 5 / 2 | 1 / 1 / 1 / 4 | 57 |
| Comp. Ex. 25 | 2-mercaptoethyl-undecyldimethylam-monium bromide | 3 | 2-mercaptoethyl-undecyldimethylam-monium bromide | 2 | 2 / 1 / 1 | 35 / 5 / 1 | 1 / 1 / 1 / 3 | 53 |

All of Examples 11 to 22 showed extremely high CO$_2$ reduction rates. Further, in Examples 11 to 22, ethylene glycol was generated with very high selectivity. Therefore, it was shown that high CO$_2$ reduction rate and selectivity were obtained even when the modified organic molecule was changed. It is considered that the ethylene glycol is generated with very high selectivity because the amino group at the terminal of the modified organic molecule promotes the reduction reaction of $CO_2$ and contributes to the improvement of the selectivity of ethylene glycol.

Comparative Examples 21 to 25 are reduction electrodes using modified organic molecules which have no amino group at their terminals. Comparative examples 21 to 25 showed relatively high $CO_2$ reduction rates, but a large amount of an acetic acid, acetaldehyde, and ethanol was generated as the reduction products.

From the above, it was shown that Examples 11 to 22 could selectively progress the $CO_2$ reduction reaction with low energy.

Example 23

The reduction catalyst was prepared in the same manner as in Example 11, except that 1-(2-mercaptoethyl)-1-(4-aminobutyl)pyrrolidinium bromide was used as a spacer organic molecule and a modified organic molecule. A three-electrode cell was produced in the same manner as described above, except that the reduction catalyst was used as a reduction electrode and a 5% $NaHCO_3$ aqueous solution was used as a $CO_2$ absorbent and an electrolyte for $CO_2$ reduction.

Example 24

A three-electrode cell was produced in the same manner as in Example 23, except that a triethanolamine aqueous solution (50 wt % aqueous solution, $CO_2$ saturated absorbing solution) was used as an electrolytic solution.

Example 25

A three-electrode cell was produced in the same manner as in Example 23, except that an aqueous solution of 90% 1-ethyl-3-methylimidazolium tetrafluoroborate ($EMIBF_4$, $CO_2$ saturated absorbing solution) was used as an electrolytic solution.

Comparative Example 26

As in Comparative Example 1, a reduction catalyst which did not have spacer organic molecules, metal fine particles, and modified organic molecules was prepared. A three-electrode cell was produced in the same manner as in Example 23, except that the reduction catalyst was used and a triethanolamine aqueous solution (50 wt % aqueous solution, $CO_2$ saturated absorbing solution) was used as an electrolytic solution.

Comparative Example 27

As in Comparative Example 1, a reduction catalyst which did not have spacer organic molecules, metal fine particles, and modified organic molecules was prepared. A three-electrode cell was produced in the same manner as in Example 23, except that the reduction catalyst was used and an aqueous solution of 90% 1-ethyl-3-methylimidazolium tetrafluoroborate ($EMIBF_4$, $CO_2$ saturated absorbing solution) was used as an electrolytic solution.

[Evaluation of $CO_2$ Reduction Performance]

For each of the three-electrode cells of Examples 23 to 25 and Comparative Examples 26 and 27, the $CO_2$ reduction performance was evaluated in the same manner as described above. The results thereof are shown in FIG. 3. For shown in Table 3.

TABLE 3

| | Spacer organic molecule | Av. particle diameter of metal fine particle (nm) | Modified organic molecule | Electrolyte | Selectivity (%) | | | | $CO_2$ reduction ratio |
|---|---|---|---|---|---|---|---|---|---|
| | | | | | CO | HCOOH HCHO $CH_3OH$ | $CH_3COOH$ $CH_3CHO$ $CH_3CH_2OH$ | Oxalic acid Glycolic acid Glycol aldehyde Ethylene glycol | |
| Ex. 23 | 1-(2-mercaptoethyl)-1-(4-aminobutyl)pyr-rolidinium bromide | 3 | 1-(2-mercaptoethyl)-1-(4-aminobutyl)pyr-rolidinium bromide | 5% $NaHCO_3$ aqueous solution | 3 | 1 1 1 | 1 1 2 | 1 1 1 62 | 75 |
| Ex. 24 | 1-(2-mercaptoethyl)-1-(4-aminobutyl)pyr-rolidinium bromide | 3 | 1-(2-mercaptoethyl)-1-(4-aminobutyl)pyr-rolidinium bromide | 50% triethanol-amine aqueous solution | 3 | 1 1 1 | 1 1 2 | 1 1 1 65 | 78 |
| Ex. 25 | 1-(2-mercaptoethyl)-1-(4-aminobutyl)pyr-rolidinium bromide | 3 | 1-(2-mercaptoethyl)-1-(4-aminobutyl)pyr-rolidinium bromide | 90% $EMIBF_4$ aqueous solution | 3 | 1 1 1 | 1 1 2 | 1 1 1 70 | 83 |
| Comp. Ex. 1 | — | — | — | 5% $NaHCO_3$ aqueous solution | 40 | — | — | — | 30 |
| Comp. Ex. 26 | — | — | — | 50% triethanol-amine aqueous solution | 40 | — | — | — | 35 |
| Comp. Ex. 27 | — | — | — | 90% $EMIBF_4$ aqueous solution | 40 | — | — | — | 38 |

All of Examples 23 to 25 showed extremely high $CO_2$ reduction rates. Further, in Examples 23 to 25, ethylene glycol was generated with very high selectivity. Therefore, it was shown that sodium hydrogen carbonate, an amine aqueous solution, and an aqueous solution of ionic liquid could be used as an electrolytic solution, and high $CO_2$ reduction rate and selectivity could be obtained, regardless of the kind of the electrolytic solution. From Example 25, it was shown that a particularly high $CO_2$ reduction rate was obtained when an aqueous solution of ionic liquid was used.

Example 26

A reduction catalyst was prepared in the same manner as in Example 11, except that a current collector was used as a substrate of a multijunction solar cell and 1-(2-mercaptoethyl)-1-(4-aminobutyl)piperidinium bromide was used as a spacer organic molecule and a modified organic molecule. An oxidation catalyst layer was formed on the surface of an oxidation electrode layer of the multijunction solar cell. Specifically, a dispersion liquid in which nano-particles of nickel oxide were dispersed in an alcoholic aqueous solution was coated on the surface of the oxidation electrode layer by spray coating. In this manner, a photochemical reaction cell of Example 26 was prepared and cut to a size of 150 mm×250 mm.

Comparative Example 28

As in Comparative Example 1, a reduction catalyst which did not have spacer organic molecules, metal fine particles, and modified organic molecules was prepared by using a substrate of a multijunction solar cell as a current collector. An oxidation catalyst layer was formed on a surface of an oxidation electrode layer of the multijunction solar cell. Specifically, a dispersion liquid in which nano-particles of nickel oxide were dispersed in an alcoholic aqueous solution was coated on the surface of the oxidation electrode layer by spray coating. In this manner, a photochemical reaction cell of Comparative Example 28 was prepared and cut to a size of 150 mm×250 mm.

[Evaluation of Energy Conversion Efficiency]

The photochemical reaction cells of Example 26 and Comparative Example 28 were incorporated into the chemical reactor, and energy conversion efficiencies thereof were evaluated. A 0.5 M aqueous solution of potassium hydroxide (KOH) was used as an oxidation-side electrolytic solution, and an aqueous solution of triethanolamine (50 wt % aqueous solution, $CO_2$ saturated absorbing liquid) was used as a reduction-side electrolytic solution. In addition, an anion exchange resin was used as an ion exchange membrane. From the oxidation catalyst layer side, light of AM 1.5 (100 mW/cm$^2$) by a solar simulator was irradiated, and all $CO_2$ reduction products generated on the reduction side were quantitatively analyzed in the same manner as in Example 1. Based on the result, energy conversion efficiency was calculated. The energy conversion efficiency was calculated by the following equation (7).

$$FE/SE \times 100 \quad (7)$$

In the formula (7), SE represents the irradiated sunlight energy, and FE represents the Gibbs free energy of the reduction product. The measurement results are shown in Table 4.

TABLE 4

| Spacer organic molecule | Av. particle diameter of metal fine particle (nm) | Modified organic molecule | Energy conversion efficiency (%) |
|---|---|---|---|
| Ex. 26 | 1-(2-mercapto-ethyl)-1-(4-aminobutyl)piperidinium bromide | 3 | 1-(2-mercapto-ethyl)-1-(4-aminobutyl)piperidinium bromide | 0.04 |

TABLE 4-continued

| Spacer organic molecule | Av. particle diameter of metal fine particle (nm) | Modified organic molecule | Energy conversion efficiency (%) |
|---|---|---|---|
| Comp. Ex. 28 | — | — | — | 0.01 |

The energy conversion efficiency of Comparative Example 28 was 0.01%. On the other hand, the energy conversion efficiency of Example 26 was 0.04%. From this, it was shown that when the reduction catalyst including the modified organic molecule was used, the reduction reaction proceeded at lower energy and the energy conversion efficiency was improved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A reduction catalyst comprising:
a current collector comprising a metal layer comprising at least one metal selected from the group consisting of Au, Ag, Cu, Zn, Pt, Fe, Ti, Ni, Sn, In, and Bi; and
organic molecules comprising a quaternary nitrogen cation, which are bonded to the metal layer and are represented by any of the following general formulae I to V:

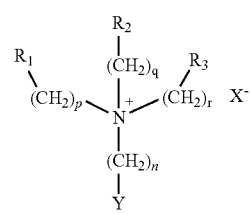

General formula I

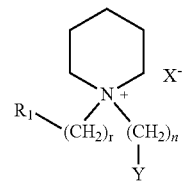

General formula II

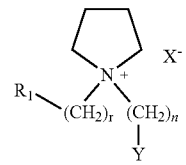

General formula III

-continued

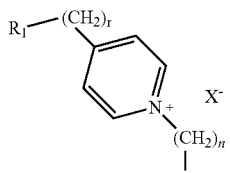
General formula IV

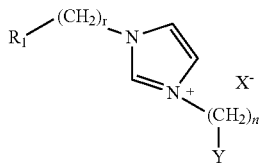
General formula V where, in the general formulae I to V, $R_1$ is a primary, secondary, or tertiary amino group, $R_2$ and $R_3$ are identical to or different from each other and are each independently H or a primary, secondary, or tertiary amino group, p, q, r, and n are each independently an integer from 1 to 12, Y is a reactive functional group selected from the group consisting of a thiol group, a disulfide group, and a thiocyanate group, and $X^-$ represents a counter anion selected from the group consisting of a fluoride ion, a chloride ion, a bromide ion, an iodide ion, $HCO_3^-$, $BF_4^-$, $PF_6^-$, $CF_3COO^-$, $CF_3SO_3^-$, $NO_3^-$, $SCN^-$, $N(CN)_2^-$, $C(CN)_3^-$ $(CF_3SO_2)_3C^-$, a bis(trifluoromethoxysulfonyl)imide anion, a bis(trifluoromethoxysulfonyl)imide anion, and a bis(perfluoroethylsulfonyl)imide anion.

2. The reduction catalyst according to claim 1, wherein, in the general formulae I to V, $R_1$ is an amino group substituted with at least one of $C_1$ to $C_{12}$ alkyl groups substituent.

3. The reduction catalyst according to claim 1, wherein the metal layer comprises metal fine particles.

4. A reduction catalyst comprising:
a current collector comprising a metal layer comprising at least one metal selected from the group consisting of Au, Ag, Cu, Zn, Pt, Fe, Ti, Ni, Sn, In, and Bi;
a spacer organic molecular layer formed on the metal layer;
metal fine particles bonded to the spacer organic molecular layer; and
organic molecules comprising a quaternary nitrogen cation, which are bonded to the metal fine particles and are represented by any of the following general formulae I to V:

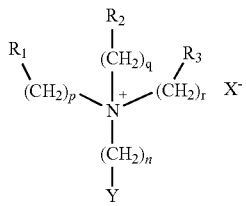
General formula I

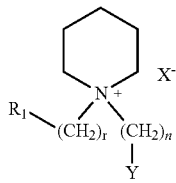
General formula II

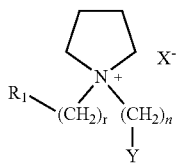
General formula III

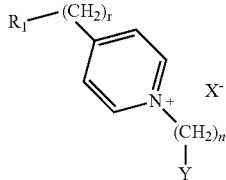
General formula IV

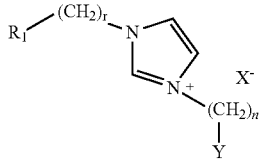
General formula V where, in the general formulae I to V, $R_1$ is a primary, secondary, or tertiary amino group, $R_2$ and $R_3$ are identical to or different from each other and are each independently H or a primary, secondary, or tertiary amino group, p, q, r, and n are each independently an integer from 1 to 12, Y is a reactive functional group selected from the group consisting of a thiol group, a disulfide group, and a thiocyanate group, and $X^-$ represents a counter anion selected from the group consisting of a fluoride ion, a chloride ion, a bromide ion, an iodide ion, $HCO_3^-$, $BF_4^-$, $PF_6^-$, $CF_3COO^-$, $CF_3SO_3^-$, $NO_3^-$, $SCN^-$, $N(CN)_2^-$, $C(CN)_3^-$ $(CF_3SO_2)_3C^-$, a bis(trifluoromethoxysulfonyl)imide anion, a bis(trifluoromethoxysulfonyl)imide anion, and a bis(perfluoroethylsulfonyl)imide anion.

5. The reduction catalyst according to claim 4, wherein, in the general formulae I to V, $R_1$ is an amino group substituted with at least one of $C_1$ to $C_{12}$ alkyl groups substituent.

6. A chemical reactor comprising:
an oxidation catalyst layer;
a reduction catalyst layer comprising the reduction catalyst according to claim 1; and
a power supply element connected to the oxidation catalyst layer and the reduction catalyst layer.

7. A chemical reactor comprising:
an oxidation catalyst layer;
a reduction catalyst layer comprising the reduction catalyst according to claim 4; and
a power supply element connected to the oxidation catalyst layer and the reduction catalyst layer.

8. The chemical reactor according to claim 6, wherein the power supply element comprises a semiconductor layer which performs charge separation by light energy.

9. The chemical reactor according to claim 7, wherein the power supply element comprises a semiconductor layer which performs charge separation by light energy.

10. The chemical reactor according to claim 8, wherein the semiconductor layer is disposed between the oxidation catalyst layer and the reduction catalyst layer.

11. The chemical reactor according to claim 9, wherein the semiconductor layer is disposed between the oxidation catalyst layer and the reduction catalyst layer.

12. A method of using a reduction catalyst, the method comprising:
   using the reduction catalyst according to claim 1 to reduce a raw material selected from the group consisting of carbon dioxide, an oxalic acid, a glycolic acid, and a glycol aldehyde to generate a product comprising ethylene glycol.

13. A method of using a reduction catalyst, the method comprising:
   using the reduction catalyst according to claim 4 to reduce a raw material selected from the group consisting of carbon dioxide, an oxalic acid, a glycolic acid, and a glycol aldehyde to generate a product comprising ethylene glycol.

* * * * *